United States Patent
Tang et al.

(10) Patent No.: US 7,371,832 B1
(45) Date of Patent: May 13, 2008

(54) POLYNUCLEOTIDES ENCODING MOLECULES ASSOCIATED WITH CELL PROLIFERATION

(75) Inventors: Y. Tom Tang, San Jose, CA (US); Preeti Lal, Santa Clara, CA (US); Jennifer L. Hillman, Mountain View, CA (US); Neil C. Corley, Castro Valley, CA (US); Chandra Arvizu, Menlo Park, CA (US); Mariah R. Baughn, San Leandro, CA (US)

(73) Assignee: Incyte Corporation, Wilmington, DE (US)

( * ) Notice: Subject to any disclaimer, the term of this patent is extended or adjusted under 35 U.S.C. 154(b) by 0 days.

(21) Appl. No.: 09/744,196

(22) PCT Filed: Jul. 21, 1999

(86) PCT No.: PCT/US99/16637

§ 371 (c)(1),
(2), (4) Date: Jan. 24, 2002

(87) PCT Pub. No.: WO00/05374

PCT Pub. Date: Feb. 3, 2000

Related U.S. Application Data

(60) Provisional application No. 60/093,827, filed on Jul. 22, 1998.

(51) Int. Cl.
*C07H 21/02* (2006.01)
*C07H 21/04* (2006.01)
*C12N 15/00* (2006.01)

(52) U.S. Cl. .................................. 536/23.1; 435/320.1
(58) Field of Classification Search ................ 530/350; 536/23.1
See application file for complete search history.

(56) References Cited

U.S. PATENT DOCUMENTS 611,090 A * 9/1898 Gorman .................... 74/483 R
6,111,090 A * 8/2000 Gorman et al. ............ 536/23.5

OTHER PUBLICATIONS

Wissmann, Christoph, et al., "WIFI, a component of the Wnt pathway, is down-regulated in prostate, breast, lung, and bladder cancer," *J. Pathol 2003*: 204-212, published online Aug. 18, 2003 in Wiley InterScience DOI: 10.1002/path.1449.

* cited by examiner

*Primary Examiner*—Stacy B. Chen
(74) *Attorney, Agent, or Firm*—Foley & Lardner LLP

(57) ABSTRACT

The invention provides human molecules associated with cell proliferation (MACP) and polynucleotides which identify and encode MACP. The invention also provides expression vectors, host cells, antibodies, agonists, and antagonists. The invention also provides methods for diagnosing, treating, or preventing disorders associated with expression of MACP.

7 Claims, No Drawings

POLYNUCLEOTIDES ENCODING MOLECULES ASSOCIATED WITH CELL PROLIFERATION

This application is a national stage filing of PCT/US99/16637, filed Jul. 21, 1999, which claims the benefit of U.S. Ser. No. 60/093,827, filed Jul. 22, 1998.

TECHNICAL FIELD

This invention relates to nucleic acid and amino acid sequences of molecules associated with cell proliferation and to the use of these sequences in the diagnosis, treatment, and prevention of cell proliferative and immune disorders.

BACKGROUND OF THE INVENTION

Tissue growth involves cell proliferation, differentiation, and apoptosis to generate functionally organized multicellular patterns. Cell proliferation has to be regulated so as to maintain both the number of cells and their spatial organization. This regulation depends on interactions of cells with one another and with the extracellular matrix. The molecules which provide this regulation fall into several categories, including growth factors, oncogenes, tumor-suppressor genes, as well as extracellular matrix and cell adhesion molecules.

Growth factors were originally described as serum factors required to promote cell proliferation. Though growth factors are present in the circulation, most act as local mediators and originate from cells in the neighborhood of the responding cell. Growth factors bind to surface receptors on the responding cell and initiate an intracellular cascade, often involving activation of kinases and phosphatases. In addition to stimulating cell division, some growth factors, such as some members of the transforming growth factor beta (TGF-β) family, act on some cells to stimulate cell proliferation and act on other cells to inhibit it. Growth factors may also stimulate a cell at one concentration and inhibit the same cell at another concentration. Most growth factors also have a multitude of other actions besides the regulation of cell growth and division: they can control the proliferation, survival, differentiation, migration, or function of cells depending on the circumstance. For example, the tumor necrosis factor/nerve growth factor (TNF/NGF) family can activate or inhibit cell death, as well as regulate proliferation and differentiation. The cell response depends on the type of cell, its stage of differentiation and transformation status, which surface receptors are stimulated, and the types of stimuli acting on the cell. (Smith, A., et al. (1994) Cell 76:959-962; and Nocentini, G., et al. (1997) Proc. Natl. Acad. Sci. USA 94:6216-6221.)

Neighboring cells in a tissue compete for growth factors, and provided with "unlimited" quantities in a perfused system will grow to even higher cell densities before reaching density-dependent inhibition of cell division. Cells often demonstrate an anchorage dependence of cell division as well. This anchorage dependence may be associated with the formation of focal contacts, linking the cytoskeleton with the extracellular matrix (ECM). The expression of ECM components can be stimulated by growth factors. For example, TGF-β stimulates fibroblasts to produce a variety of ECM proteins, including fibronectin, collagen, and tenascin. (Pearson, C. A., et al. (1988) EMBO J. 7:2677-2981.) In fact, for some cell types specific ECM molecules, such as laminin or fibronectin, may act as growth factors. Tenascin-C and -R, expressed in developing and lesioned neural tissue, provide stimulatory/anti-adhesive or inhibitory properties, respectively, for axonal growth. (Faissner, A. (1997) Cell Tissue Res 290:331-341.)

Oncogenes (i.e. "cancer-causing genes") are involved in reception and activation of growth factor signals. Mutations which hyperactivate oncogenes result in cell proliferation. Stimulation of a cell by growth factors activates two sets of gene products, the early-response genes and the delayed-response genes. Early-response gene products include myc, fos, and jun, all of which encode gene regulatory proteins. These regulatory proteins lead to the transcriptional activation of a second set of genes, the delayed-response genes, which include the cell-cycle regulators Cdk and cyclins. For example, the human T-cell leukemia virus type 1 (HTLV-1) Tax transactivator protein acts as an early response gene by enhancing the activity of a cellular transcription factor. The oncogenic properties of the Tax protein include transformation of primary T-lymphocytes and fibroblasts through cooperation with the a GTP-binding protein, Ras. Recently investigators have shown that Tax interacts with several PDZ-containing proteins. The PDZ domain, originally described in the *Drosophila* tumor suppressor protein Discs-Large, is common to membrane proteins thought to be involved in clustering receptors in growth factor signal transduction pathways. (Rousset, R., et al. (1998) Oncogene 16, 643-654.)

Tumor-suppressor genes are involved in inhibiting cell proliferation. Mutations which cause reduced or loss of function in tumor-suppressor genes result in cell proliferation. For example, the retinoblastoma gene product (RB), in a non-phosphorylated state, binds several early-response genes and suppresses their transcription, thus blocking cell division. Phosphorylation of RB causes it to dissociate from the genes, releasing the suppression, and allowing cell division to proceed.

Other gene products involved in cell proliferation, differentiation, and apoptosis are yet to be discovered. One method currently being utilized to help identify such new molecules involves comparison between quiescent and proliferative tissues. For example, a subtractive hybridization screen of human placental cytotrophoblast cells identified 20 genes whose expression levels rose due to EGF induction of cell proliferation. (Morrish, D. W., et al. (1996) Placenta 17:431-441.) Another method involves identification of molecules produced in cells treated with anti-tumorigenic agents, such as dithiolethiones. Presumably, the protective action of these anti-tumorigenic agents is associated with the induction of tumor suppressor gene products. (Primiano, T. et al. (1996) Carcinogenesis 17:2297-2303.)

The discovery of new molecules associated with cell proliferation and the polynucleotides encoding them satisfies a need in the art by providing new compositions which are useful in the diagnosis, treatment, and prevention of cell proliferative and immune disorders.

SUMMARY OF THE INVENTION

The invention features substantially purified polypeptides, molecules associated with cell proliferation, referred to collectively as "MACP" and individually as "MACP-1", "MACP-2", "MACP-3", "MACP-4" and "MACP-5". In one aspect, the invention provides a substantially purified polypeptide comprising an amino acid sequence selected from the group consisting of SEQ ID NO:1, SEQ ID NO:2, SEQ ID NO:3, SEQ ID NO:4, SEQ ID NO:5 (SEQ ID NO:1 through 5), and fragments thereof.

The invention further provides a substantially purified variant having at least 90% amino acid identity to the amino acid sequences of SEQ ID NO:1, SEQ ID NO:2, SEQ ID NO:3, SEQ ID NO:4, or SEQ ID NO:5, or to a fragment of any of these sequences. The invention also provides an isolated and purified polynucleotide encoding the polypeptide comprising an amino acid sequence selected from the group consisting of SEQ ID NO:1 through 5, and fragments thereof. The invention also includes an isolated and purified polynucleotide variant having at least 90% polynucleotide sequence identity to the polynucleotide encoding the polypeptide comprising an amino acid sequence selected from the group consisting of SEQ ID NO:1 through 5, and fragments thereof.

Additionally, the invention provides an isolated and purified polynucleotide which hybridizes under stringent conditions to the polynucleotide encoding the polypeptide comprising an amino acid sequence selected from the group consisting of SEQ ID NO:1 through 5, and fragments thereof, as well as an isolated and purified polynucleotide having a sequence which is complementary to the polynucleotide encoding the polypeptide comprising the amino acid sequence selected from the group consisting of SEQ ID NO:1 through 5, and fragments thereof.

The invention also provides an isolated and purified polynucleotide comprising a polynucleotide sequence selected from the group consisting of SEQ ID NO:6. SEQ ID NO:7, SEQ ID NO:8, SEQ ID NO:9. SEQ ID NO:10 (SEQ ID NO:6 through 10), and fragments thereof. The invention further provides an isolated and purified polynucleotide variant having at least 90% polynucleotide sequence identity to the polynucleotide sequence comprising a polynucleotide sequence selected from the group consisting of SEQ ID NO:6 through 10, and fragments thereof, as well as an isolated and purified polynucleotide having a sequence which is complementary to the polynucleotide comprising a polynucleotide sequence selected from the group consisting of SEQ ID NO:6 through 10, and fragments thereof.

The invention further provides an expression vector containing at least a fragment of the polynucleotide encoding the polypeptide comprising an amino acid sequence selected from the group consisting of SEQ ID NO:1 through 5, and fragments thereof. In another aspect, the expression vector is contained within a host cell.

The invention also provides a method for producing a polypeptide comprising the amino acid sequence selected from the group consisting of SEQ ID NO:1 through 5, and fragments thereof, the method comprising the steps of: (a) culturing the host cell containing an expression vector containing at least a fragment of a polynucleotide encoding the polypeptide under conditions suitable for the expression of the polypeptide: and (b) recovering the polypeptide from the host cell culture.

The invention also provides a pharmaceutical composition comprising a substantially purified polypeptide having the amino acid sequence selected from the group consisting of SEQ ID NO:1 through 5, and fragments thereof in conjunction with a suitable pharmaceutical carrier.

The invention further includes a purified antibody which binds to a polypeptide comprising the amino acid sequence selected from the group consisting of SEQ ID NO:1 through 5, and fragments thereof, as well as a purified agonist and a purified antagonist to the polypeptide.

The invention also provides a method for treating or preventing a cell proliferative disorder associated with decreased expression or activity of MACP, the method comprising administering to a subject in need of such treatment an effective amount of a pharmaceutical composition comprising a substantially purified polypeptide having an amino acid sequence selected from the group consisting of SEQ ID NO:1 through 5, and fragments thereof.

The invention also provides a method for treating or preventing a cell proliferative disorder associated with increased expression or activity of MACP, the method comprising administering to a subject in need of such treatment an effective amount of an antagonist of the polypeptide having an amino acid sequence selected from the group consisting of SEQ ID NO:1 through 5, and fragments thereof.

The invention also provides a method for treating or preventing an immune disorder, the method comprising administering to a subject in need of such treatment an effective amount of a pharmaceutical composition comprising a substantially purified polypeptide having an amino acid sequence selected from the group consisting of SEQ ID NO:1 through 5, and fragments thereof.

The invention also provides a method for detecting a polynucleotide encoding the polypeptide comprising the amino acid sequence selected from the group consisting of SEQ ID NO:1 through 5, and fragments thereof in a biological sample containing nucleic acids, the method comprising the steps of: (a) hybridizing the complement of the polynucleotide sequence encoding the polypeptide comprising the amino acid sequence selected from the group consisting of SEQ ID NO:1 through 5, and fragments thereof to at least one of the nucleic acids of the biological sample, thereby forming a hybridization complex: and (b) detecting the hybridization complex, wherein the presence of the hybridization complex correlates with the presence of a polynucleotide encoding the polypeptide in the biological sample. In one aspect, the method further comprises amplifying the polynucleotide prior to hybridization.

BRIEF DESCRIPTION OF THE TABLES

Table 1 shows in columns 1 and 2 the sequence identification numbers (SEQ ID NO:) of the amino acid sequences and corresponding nucleotide sequences, respectively. Column 3 shows the Incyte Clone number in which nucleic acids encoding MACP were first identified using a computer search, e.g. BLAST, for amino acid sequence alignments. Column 4 shows the clones and shotgun sequences, and the cDNA libraries from which they were isolated, which were used to derive the consensus of the nucleotide sequence for each of the MACP disclosed herein.

Table 2 shows various properties of the polypeptides of the invention including the number of amino acid residues, potential phosphorylation and glycosylation sites, the identity of the protein, and the methods used to identify the protein through sequence homologies and protein motifs.

Table 3 shows the tissue expression of each nucleic acid sequence by northern analysis, the diseases or disorders associated with this tissue expression, and the vector into which each cDNA sequence was cloned.

Table 4 shows the Incyte Clone numbers, the cDNA library from which they were derived, and a description of the library including the source of the RNA and the vector used in the construction of the library.

Table 5 summarizes the software programs, corresponding algorithms, references, and cutoff parameters used to analyze ESTs and full length polynucleotide and amino acid sequences where applicable.

DESCRIPTION OF THE INVENTION

Before the present proteins, nucleotide sequences, and methods are described, it is understood that this invention is not limited to the particular methodology, protocols, cell lines, vectors, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a," "an," and "the" include plural reference unless the context clearly dictates otherwise. Thus, for example, a reference to "a host cell" includes a plurality of such host cells, and a reference to "an antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are cited for the purpose of describing and disclosing the cell lines, vectors, and methodologies which are reported in the publications and which might be used in connection with the invention. Nothing herein is to be construed as an admission that the invention is not entitled to antedate such disclosure by virtue of prior invention.

DEFINITIONS

"MACP." as used herein, refers to the amino acid sequences, or variant thereof, of substantially purified MACP obtained from any species, particularly a mammalian species, including bovine, ovine, porcine, murine, equine, and preferably the human species, from any source, whether natural, synthetic, semi-synthetic, or recombinant.

The term "agonist," as used herein, refers to a molecule which, when bound to MACP, increases or prolongs the duration of the effect of MACP. Agonists may include proteins, nucleic acids, carbohydrates, or any other molecules which bind to and modulate the effect of MACP.

An "allelic variant," as this term is used herein, is an alternative form of the gene encoding MACP. Allelic variants may result from at least one mutation in the nucleic acid sequence and may result in altered mRNAs or in polypeptides whose structure or function may or may not be altered. Any given natural or recombinant gene may have none, one, or many allelic forms. Common mutational changes which give rise to allelic variants are generally ascribed to natural deletions, additions, or substitutions of nucleotides. Each of these types of changes may occur alone, or in combination with the others, one or more times in a given sequence.

"Altered" nucleic acid sequences encoding MACP, as described herein, include those sequences with deletions, insertions, or substitutions of different nucleotides, resulting in a polynucleotide the same as MACP or a polypeptide with at least one functional characteristic of MACP. Included within this definition are polymorphisms which may or may not be readily detectable using a particular oligonucleotide probe of the polynucleotide encoding MACP, and improper or unexpected hybridization to allelic variants, with a locus other than the normal chromosomal locus for the polynucleotide sequence encoding MACP. The encoded protein may also be "altered," and may contain deletions, insertions, or substitutions of amino acid residues which produce a silent change and result in a functionally equivalent MACP. Deliberate amino acid substitutions may be made on the basis of similarity in polarity, charge, solubility, hydrophobicity, hydrophilicity, and/or the amphipathic nature of the residues, as long as the biological or immunological activity of MACP is retained. For example, negatively charged amino acids may include aspartic acid and glutamic acid, positively charged amino acids may include lysine and arginine, and amino acids with uncharged polar head groups having similar hydrophilicity values may include leucine, isoleucine, and valine; glycine and alanine; asparagine and glutamine; serine and threonine; and phenylalanine and tyrosine.

The terms "amino acid" or "amino acid sequence," as used herein, refer to an oligopeptide, peptide, polypeptide, or protein sequence, or a fragment of any of these, and to naturally occurring or synthetic molecules. In this context, "fragments," "immunogenic fragments," or "antigenic fragments" refer to fragments of MACP which are preferably at least 5 to about 15 amino acids in length, most preferably at least 14 amino acids, and which retain some biological activity or immunological activity of MACP. Where "amino acid sequence" is recited herein to refer to an amino acid sequence of a naturally occurring protein molecule, "amino acid sequence" and like terms are not meant to limit the amino acid sequence to the complete native amino acid sequence associated with the recited protein molecule.

"Amplification," as used herein, relates to the production of additional copies of a nucleic acid sequence. Amplification is generally carried out using polymerase chain reaction (PCR) technologies well known in the art. (See, e.g., Dieffenbach, C. W. and G. S. Dveksler (1995) *PCR Primer, a Laboratory Manual*, Cold Spring Harbor Press, Plainview. N.Y., pp. 1-5.)

The term "antagonist." as it is used herein, refers to a molecule which, when bound to MACP decreases the amount or the duration of the effect of the biological or immunological activity of MACP. Antagonists may include proteins, nucleic acids, carbohydrates, antibodies, or any other molecules which decrease the effect of MACP.

As used herein, the term antibody refers to intact molecules as well as to fragments thereof, such as Fab, F(ab')$_2$, and Fv fragments, which are capable of binding the epitopic determinant. Antibodies that bind MACP polypeptides can be prepared using intact polypeptides or using fragments containing small peptides of interest as the immunizing antigen. The polypeptide or oligopeptide used to immunize an animal (e.g., a mouse, a rat, or a rabbit) can be derived from the translation of RNA, or synthesized chemically, and can be conjugated to a carrier protein if desired. Commonly used carriers that are chemically coupled to peptides include bovine serum albumin, thyroglobulin, and keyhole limpet hemocyanin (KLH). The coupled peptide is then used to immunize the animal.

The term "antigenic determinant." as used herein, refers to that fragment of a molecule (i.e., an epitope) that makes contact with a particular antibody. When a protein or a fragment of a protein is used to immunize a host animal, numerous regions of the protein may induce the production of antibodies which bind specifically to antigenic determinants (given regions or three-dimensional structures on the protein). An antigenic determinant may compete with the intact antigen (i.e., the immunogen used to elicit the immune response) for binding to an antibody.

The term "antisense," as used herein, refers to any composition containing a nucleic acid sequence which is complementary to the "sense" strand of a specific nucleic acid sequence. Antisense molecules may be produced by any method including synthesis or transcription. Once introduced into a cell, the complementary nucleotides combine with natural sequences produced by the cell to form duplexes and to block either transcription or translation. The designation "negative" can refer to the antisense strand, and the designation "positive" can refer to the sense strand.

As used herein, the term "biologically active," refers to a protein having structural, regulatory, or biochemical functions of a naturally occurring molecule. Likewise, "immunologically active" refers to the capability of the natural, recombinant, or synthetic MACP, or of any oligopeptide thereof, to induce a specific immune response in appropriate animals or cells and to bind with specific antibodies.

The terms "complementary" or "complementarity," as used herein, refer to the natural binding of polynucleotides by base pairing. For example, the sequence "5' A-G-T 3'" binds to the complementary sequence "3' T-C-A 5'." Complementarity between two single-stranded molecules may be "partial." such that only some of the nucleic acids bind, or it may be "complete." such that total complementarity exists between the single stranded molecules. The degree of complementarity between nucleic acid strands has significant effects on the efficiency and strength of the hybridization between the nucleic acid strands. This is of particular importance in amplification reactions, which depend upon binding between nucleic acids strands, and in the design and use of peptide nucleic acid (PNA) molecules.

A "composition comprising a given polynucleotide sequence" or a "composition comprising a given amino acid sequence," as these terms are used herein, refer broadly to any composition containing the given polynucleotide or amino acid sequence. The composition may comprise a dry formulation or an aqueous solution. Compositions comprising polynucleotide sequences encoding MACP or fragments of MACP may be employed as hybridization probes. The probes may be stored in freeze-dried form and may be associated with a stabilizing agent such as a carbohydrate. In hybridizations, the probe may be deployed in an aqueous solution containing salts, e.g., NaCl, detergents. e.g., sodium dodecyl sulfate (SDS), and other components, e.g., Denhardt's solution, dry milk, salmon sperm DNA, etc.

"Consensus sequence," as used herein, refers to a nucleic acid sequence which has been resequenced to resolve uncalled bases, extended using XL-PCR™ (The Perkin-Elmer Corp., Norwalk, Conn.) in the 5' and/or the 3' direction, and resequenced, or which has been assembled from the overlapping sequences of more than one Incyte Clone using a computer program for fragment assembly, such as the GELVIEW™ Fragment Assembly system (GCG, Madison, Wis.). Some sequences have been both extended and assembled to produce the consensus sequence.

As used herein, the term "correlates with expression of a polynucleotide" indicates that the detection of the presence of nucleic acids, the same or related to a nucleic acid sequence encoding MACP, by Northern analysis is indicative of the presence of nucleic acids encoding MACP in a sample, and thereby correlates with expression of the transcript from the polynucleotide encoding MACP.

A "deletion," as the term is used herein, refers to a change in the amino acid or nucleotide sequence that results in the absence of one or more amino acid residues or nucleotides.

The term "derivative," as used herein, refers to the chemical modification of a polypeptide sequence, or a polynucleotide sequence. Chemical modifications of a polynucleotide sequence can include, for example, replacement of hydrogen by an alkyl, acyl, or amino group. A derivative polynucleotide encodes a polypeptide which retains at least one biological or immunological function of the natural molecule. A derivative polypeptide is one modified by glycosylation, pegylation, or any similar process that retains at least one biological or immunological function of the polypeptide from which it was derived.

The term "similarity," as used herein, refers to a degree of complementarity. There may be partial similarity or complete similarity. The word "identity" may substitute for the word "similarity." A partially complementary sequence that at least partially inhibits an identical sequence from hybridizing to a target nucleic acid is referred to as "substantially similar." The inhibition of hybridization of the completely complementary sequence to the target sequence may be examined using a hybridization assay (Southern or Northern blot, solution hybridization, and the like) under conditions of reduced stringency. A substantially similar sequence or hybridization probe will compete for and inhibit the binding of a completely similar (identical) sequence to the target sequence under conditions of reduced stringency. This is not to say that conditions of reduced stringency are such that non-specific binding is permitted, as reduced stringency conditions require that the binding of two sequences to one another be a specific (i.e. a selective) interaction. The absence of non-specific binding may be tested by the use of a second target sequence which lacks even a partial degree of complementarity (e.g., less than about 30% similarity or identity). In the absence of non-specific binding, the substantially similar sequence or probe will not hybridize to the second non-complementary target sequence.

The phrases "percent identity" or "% identity" refer to the percentage of sequence similarity found in a comparison of two or more amino acid or nucleic acid sequences. Percent identity can be determined electronically, e.g., by using the MegAlign™ program (DNASTAR, Inc., Madison Wis.). The MegAlign™ program can create alignments between two or more sequences according to different methods, e.g., the clustal method. (See, e.g., Higgins, D. G. and P. M. Sharp (1988) Gene 73:237-244.) The clustal algorithm groups sequences into clusters by examining the distances between all pairs. The clusters are aligned pairwise and then in groups. The percentage similarity between two amino acid sequences, e.g., sequence A and sequence B, is calculated by dividing the length of sequence A, minus the number of gap residues in sequence A, minus the number of gap residues in sequence B, into the sum of the residue matches between sequence A and sequence B, times one hundred. Gaps of low or of no similarity between the two amino acid sequences are not included in determining percentage similarity. Percent identity between nucleic acid sequences can also be counted or calculated by other methods known in the art, e.g., the Jotun Hein method. (See, e.g., Hein, J. (1990) Methods Enzymol. 183:626-645.) Identity between sequences can also be determined by other methods known in the art, e.g., by varying hybridization conditions.

"Human artificial chromosomes" (HACs), as described herein, are linear microchromosomes which may contain DNA sequences of about 6 kb to 10 Mb in size, and which contain all of the elements required for stable mitotic chromosome segregation and maintenance. (See, e.g., Harrington, J. J. et al. (1997) Nat Genet. 15:345-355.)

The term "humanized antibody," as used herein, refers to antibody molecules in which the amino acid sequence in the non-antigen binding regions has been altered so that the antibody more closely resembles a human antibody, and still retains its original binding ability.

'Hybridization,' as the term is used herein, refers to any process by which a strand of nucleic acid binds with a complementary strand through base pairing.

As used herein, the term "hybridization complex" refers to a complex formed between two nucleic acid sequences by virtue of the formation of hydrogen bonds between complementary bases. A hybridization complex may be formed in solution (e.g., $C_0t$ or $R_0t$ analysis) or formed between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

The words "insertion" or "addition," as used herein, refer to changes in an amino acid or nucleotide sequence resulting in the addition of one or more amino acid residues or nucleotides, respectively, to the sequence found in the naturally occurring molecule.

"Immune response" can refer to conditions associated with inflammation, trauma, immune disorders, or infectious or genetic disease, etc. These conditions can be characterized by expression of various factors, e.g., cytokines, chemokines, and other signaling molecules, which may affect cellular and systemic defense systems.

The term "microarray," as used herein, refers to an arrangement of distinct polynucleotides arrayed on a substrate, e.g., paper, nylon or any other type of membrane, filter, chip, glass slide, or any other suitable solid support.

The terms "element" or "array element" as used herein in a microarray context, refer to hybridizable polynucleotides arranged on the surface of a substrate.

The term "modulate." as it appears herein, refers to a change in the activity of MACP. For example, modulation may cause an increase or a decrease in protein activity, binding characteristics, or any other biological, functional, or immunological properties of MACP.

The phrases "nucleic acid" or "nucleic acid sequence," as used herein, refer to a nucleotide, oligonucleotide, polynucleotide, or any fragment thereof. These phrases also refer to DNA or RNA of genomic or synthetic origin which may be single-stranded or double-stranded and may represent the sense or the antisense strand, to peptide nucleic acid (PNA), or to any DNA-like or RNA-like material. In this context, "fragments" refers to those nucleic acid sequences which, comprise a region of unique polynucleotide sequence that specifically identifies SEQ ID NO:6-10, for example, as distinct from any other sequence in the same genome. For example, a fragment of SEQ ID NO:6-10 is useful in hybridization and amplification technologies and in analogous methods that distinguish SEQ ID NO:6-10 from related polynucleotide sequences. A fragment of SEQ ID NO:6-10 is at least about 15-20 nucleotides in length. The precise length of the fragment of SEQ ID NO:6-10 and the region of SEQ ID NO:6-10 to which the fragment corresponds are routinely determinable by one of ordinary skill in the art based on the intended purpose for the fragment. In some cases, a fragment, when translated, would produce polypeptides retaining some functional characteristic, e.g., antigenicity, or structural domain characteristic, e.g., ATP-binding site, of the full-length polypeptide.

The terms "operably associated" or "operably linked," as used herein, refer to functionally related nucleic acid sequences. A promoter is operably associated or operably linked with a coding sequence if the promoter controls the translation of the encoded polypeptide. While operably associated or operably linked nucleic acid sequences can be contiguous and in the same reading frame, certain genetic elements, e.g., repressor genes, are not contiguously linked to the sequence encoding the polypeptide but still bind to operator sequences that control expression of the polypeptide.

The term "oligonucleotide," as used herein, refers to a nucleic acid sequence of at least about 6 nucleotides to 60 nucleotides, preferably about 15 to 30 nucleotides, and most preferably about 20 to 25 nucleotides, which can be used in PCR amplification or in a hybridization assay or microarray. As used herein, the term "oligonucleotide" is substantially equivalent to the terms "amplimer," "primer," "oligomer," and "probe," as these terms are commonly defined in the art.

"Peptide nucleic acid" (PNA), as used herein, refers to an antisense molecule or anti-gene agent which comprises an oligonucleotide of at least about 5 nucleotides in length linked to a peptide backbone of amino acid residues ending in lysine. The terminal lysine confers solubility to the composition. PNAs preferentially bind complementary single stranded DNA or RNA and stop transcript elongation, and may be pegylated to extend their lifespan in the cell. (See, e.g., Nielsen, P. E. et al. (1993) Anticancer Drug Des. 8:53-63.)

The term "sample," as used herein, is used in its broadest sense. A biological sample suspected of containing nucleic acids encoding MACP, or fragments thereof, or MACP itself, may comprise a bodily fluid; an extract from a cell, chromosome, organelle, or membrane isolated from a cell; a cell; genomic DNA, RNA, or cDNA, in solution or bound to a solid support; a tissue; a tissue print; etc.

As used herein, the terms "specific binding" or "specifically binding" refer to that interaction between a protein or peptide and an agonist, an antibody, or an antagonist. The interaction is dependent upon the presence of a particular structure of the protein, e.g., the antigenic determinant or epitope, recognized by the binding molecule. For example, if an antibody is specific for epitope "A." the presence of a polypeptide containing the epitope A, or the presence of free unlabeled A, in a reaction containing free labeled A and the antibody will reduce the amount of labeled A that binds to the antibody.

As used herein, the term "stringent conditions" refers to conditions which permit hybridization between polynucleotides and the claimed polynucleotides. Stringent conditions can be defined by salt concentration, the concentration of organic solvent, e.g., formamide, temperature, and other conditions well known in the art. In particular, stringency can be increased by reducing the concentration of salt, increasing the concentration of formamide, or raising the hybridization temperature.

The term "substantially purified." as used herein, refers to nucleic acid or amino acid sequences that are removed from their natural environment and are isolated or separated, and are at least about 60% free, preferably about 75% free, and most preferably about 90% free from other components with which they are naturally associated.

A "substitution," as used herein, refers to the replacement of one or more amino acids or nucleotides by different amino acids or nucleotides, respectively.

"Transformation," as defined herein, describes a process by which exogenous DNA enters and changes a recipient cell. Transformation may occur under natural or artificial conditions according to various methods well known in the art, and may rely on any known method for the insertion of foreign nucleic acid sequences into a prokaryotic or eukaryotic host cell. The method for transformation is selected based on the type of host cell being transformed and may include, but is not limited to, viral infection, electroporation, heat shock, lipofection, and particle bombardment. The term "transformed" cells includes stably transformed cells in which the inserted DNA is capable of replication either as an autonomously replicating plasmid or as part of the host chromosome, as well as transiently transformed cells which express the inserted DNA or RNA for limited periods of time.

A "variant" of MACP polypeptides, as used herein, refers to an amino acid sequence that is altered by one or more amino acid residues. The variant may have "conservative" changes, wherein a substituted amino acid has similar structural or chemical properties (e.g., replacement of leucine with isoleucine). More rarely, a variant may have "nonconservative" changes (e.g., replacement of glycine with tryptophan). Analogous minor variations may also include amino acid deletions or insertions, or both. Guidance in determining which amino acid residues may be substituted, inserted, or deleted without abolishing biological or immunological activity may be found using computer programs well known in the art, for example. LASERGENE™ software.

The term "variant," when used in the context of a polynucleotide sequence, may encompass a polynucleotide sequence related to MACP. This definition may also include, for example, "allelic" (as defined above), "splice," "species," or "polymorphic" variants. A splice variant may have significant identity to a reference molecule, but will generally have a greater or lesser number of polynucleotides due to alternate splicing of exons during mRNA processing. The corresponding polypeptide may possess additional functional domains or an absence of domains. Species variants are polynucleotide sequences that vary from one species to another. The resulting polypeptides generally will have significant amino acid identity relative to each other. A polymorphic variant is a variation in the polynucleotide sequence of a particular gene between individuals of a given species. Polymorphic variants also may encompass "single nucleotide polymorphisms" (SNPs) in which the polynucleotide sequence varies by one base. The presence of SNPs may be indicative of, for example, a certain population, a disease state, or a propensity for a disease state.

THE INVENTION

The invention is based on the discovery of new molecules associated with cell proliferation (MACP), the polynucleotides encoding MACP, and the use of these compositions for the diagnosis, treatment, or prevention of cell proliferative and immune disorders.

Table 1 shows in columns 1 and 2 the sequence identification numbers (SEQ ID NO) of the amino acid sequences and corresponding nucleotide sequences, respectively. Column 3 shows the incyte Clone number in which nucleic acids encoding MACP were first identified using a computer search, e.g. BLAST, for amino acid sequence alignments. Column 4 shows the clones and shotgun sequences, and the cDNA libraries from which they were isolated, which were used to derive the consensus of the nucleotide sequence for each of the MACP disclosed herein.

Table 2 shows various properties of the polypeptides of the invention including the number of amino acid residues, potential phosphorylation and glycosylation sites, the identity of the protein, and the methods used to identify the protein through sequence homologies and protein motifs.

Table 3 shows the tissue expression of each nucleic acid sequence by northern analysis, diseases or disorders associated with this tissue expression, and the vector into which each cDNA sequence was cloned.

The invention also encompasses MACP variants. A preferred MACP variant is one which has at least about 80%, more preferably at least about 90%, and most preferably at least about 95% amino acid sequence identity to the MACP amino acid sequence, and which contains at least one functional or structural characteristic of MACP.

The invention also encompasses polynucleotides which encode MACP. In a particular embodiment, the invention encompasses a polynucleotide sequence comprising a sequence selected from the group consisting of SEQ ID NO:6 through 10.

The invention also encompasses a variant of a polynucleotide sequence encoding MACP. In particular, such a variant polynucleotide sequence will have at least about 70%, more preferably at least about 85%, and most preferably at least about 95% polynucleotide sequence identity to the polynucleotide sequence encoding MACP. A particular aspect of the invention encompasses a variant of a polynucleotide sequence comprising a sequence selected from the group of SEQ ID NO:6 through 10 which has at least about 70%, more preferably at least about 85%, and most preferably at least about 95% polynucleotide sequence identity to a nucleotide sequence selected from the group consisting of SEQ ID NO:6 through 10. Any one of the polynucleotide variants described above can encode an amino acid sequence which contains at least one functional or structural characteristic of MACP.

It will be appreciated by those skilled in the art that as a result of the degeneracy of the genetic code, a multitude of polynucleotide sequences encoding MACP, some bearing minimal similarity to the polynucleotide sequences of any known and naturally occurring gene, may be produced. Thus, the invention contemplates each and every possible variation of polynucleotide sequence that could be made by selecting combinations based on possible codon choices. These combinations are made in accordance with the standard triplet genetic code as applied to the polynucleotide sequence of naturally occurring MACP, and all such variations are to be considered as being specifically disclosed.

Although nucleotide sequences which encode MACP and its variants are preferably capable of hybridizing to the nucleotide sequence of the naturally occurring MACP under appropriately selected conditions of stringency, it may be advantageous to produce nucleotide sequences encoding MACP possessing a substantially different codon usage, e.g., inclusion of non-naturally occurring codons. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding MACP and its derivatives without altering the encoded amino acid sequences include the production of RNA transcripts having more desirable properties, such as a greater half-life, than transcripts produced from the naturally occurring sequence.

The invention also encompasses production of DNA sequences which encode MACP and MACP derivatives, or fragments thereof, entirely by synthetic chemistry. After production, the synthetic sequence may be inserted into any of the many available expression vectors and cell systems using reagents well known in the art. Moreover, synthetic chemistry may be used to introduce mutations into a sequence encoding MACP or any fragment thereof.

Also encompassed by the invention are polynucleotide sequences that are capable of hybridizing to the claimed polynucleotide sequences, and, in particular, to those shown in SEQ ID NO:6 through 10 and fragments thereof, under various conditions of stringency. (See, e.g., Wahl, G. M. and S. L. Berger (1987) Methods Enzymol. 152:399-407; Kimmel, A. R. (1987) Methods Enzymol. 152:507-511.) For example, stringent salt concentration will ordinarily be less than about 750 mM NaCl and 75 mM trisodium citrate, preferably less than about 500 mM NaCl and 50 mM trisodium citrate, and most preferably less than about 250 mM NaCl and 25 mM trisodium citrate. Low stringency hybridization can be obtained in the absence of organic solvent. e.g., formamide, while high stringency hybridization can be obtained in the presence of at least about 35% formamide, and most preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 µg/ml denatured salmon sperm DNA (ssDNA). In a most preferred embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

The washing steps which follow hybridization can also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include temperature of at least about 25° C., more preferably of at least about 42° C., and most preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a most preferred embodiment, wash steps will occur at 68° C. in 15 mM NaCl, 1.5 mM trisodium citrate, and 0.1% SDS. Additional variations on these conditions will be readily apparent to those skilled in the art.

Methods for DNA sequencing and analysis are well known in the art. The methods may employ such enzymes as the Klenow fragment of DNA polymerase I. SEQUENASE® (Amersham Pharmacia Biotech Ltd. Uppsala. Sweden), Taq polymerase (The Perkin-Elmer Corp., Norwalk, Conn.), thermostable T7 polymerase (Amersham Pharmacia Biotech Ltd., Uppsala, Sweden), or combinations of polymerases and proofreading exonucleases, such as those found in the ELONGASE™ amplification system (Life Technologies, Inc., Rockville, Md.). Preferably, sequence preparation is automated with machines, e.g., the ABI CATALYST™ 800 (The Perkin-Elmer Corp., Norwalk, Conn.) or MICRO-LAB® 2200 (Hamilton Co., Reno, Nev.) systems, in combination with thermal cyclers. Sequencing can also be automated, such as by ABI PRISM™ 373 or 377 systems (The Perkin-Elmer Corp., Norwalk, Conn.) or the MEGABACE™ 1000 capillary electrophoresis system (Molecular Dynamics, Inc., Sunnyvale, Calif.). Sequences can be analyzed using computer programs and algorithms well known in the art. (See, e.g., Ausubel, supra, unit 7.7; and Meyers, R. A. (1995) Molecular Biology and Biotechnology, Wiley VCH, Inc, New York, N.Y.)

The nucleic acid sequences encoding MACP may be extended utilizing a partial nucleotide sequence and employing various PCR-based methods known in the art to detect upstream sequences, such as promoters and regulatory elements. For example, one method which may be employed, restriction-site PCR, uses universal and nested primers to amplify unknown sequence from genomic DNA within a cloning vector. (See, e.g., Sarkar, G. (1993) PCR Methods Applic. 2:318-322.) Another method, inverse PCR, uses primers that extend in divergent directions to amplify unknown sequence from a circularized template. The template is derived from restriction fragments comprising a known genomic locus and surrounding sequences. (See, e.g., Triglia, T. et al. (1988) Nucleic Acids Res. 16:8186.) A third method, capture PCR, involves PCR amplification of DNA fragments adjacent to known sequences in human and yeast artificial chromosome DNA. (See, e.g., Lagerstrom, M. et al. (1991) PCR Methods Applic. 1:111-119.) In this method, multiple restriction enzyme digestions and ligations may be used to insert an engineered double-stranded sequence into a region of unknown sequence before performing PCR. Other methods which may be used to retrieve unknown sequences are known in the art. (See, e.g., Parker, J. D. et al. (1991) Nucleic Acids Res. 19:3055-306). Additionally, one may use PCR, nested primers, and PromoterFinder™ libraries (Clontech, Palo Alto. CA) to walk genomic DNA. This procedure avoids the need to screen libraries and is useful in finding intron/exon junctions. For all PCR-based methods, primers may be designed using commercially available software, such as OLIGO™ 4.06 Primer Analysis software (National Biosciences Inc., Plymouth, Minn.) or another appropriate program, to be about 22 to 30 nucleotides in length, to have a GC content of about 50% or more, and to anneal to the template at temperatures of about 68° C. to 72° C.

When screening for full-length cDNAs, it is preferable to use libraries that have been size-selected to include larger cDNAs. In addition, random-primed libraries, which often include sequences containing the 5' regions of genes, are preferable for situations in which an oligo d(T) library does not yield a full-length cDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different nucleotide-specific, laser-stimulated fluorescent dyes, and a charge coupled device camera for detection of the emitted wavelengths. Output/light intensity may be converted to electrical signal using appropriate software (e.g., Genotyper™ and Sequence Navigator™, (The Perkin-Elmer Corp., Norwalk, Conn.)), and the entire process from loading of samples to computer analysis and electronic data display may be computer controlled. Capillary electrophoresis is especially preferable for sequencing small DNA fragments which may be present in limited amounts in a particular sample.

In another embodiment of the invention, polynucleotide sequences or fragments thereof which encode MACP may be cloned in recombinant DNA molecules that direct expression of MACP, or fragments or functional equivalents thereof, in appropriate host cells. Due to the inherent degeneracy of the genetic code, other DNA sequences which encode substantially the same or a functionally equivalent amino acid sequence may be produced and used to express MACP.

The nucleotide sequences of the present invention can be engineered using methods generally known in the art in order to alter MACP-encoding sequences for a variety of purposes including, but not limited to, modification of the cloning, processing, and/or expression of the gene product. DNA shuffling by random fragmentation and PCR reassembly of gene fragments and synthetic oligonucleotides may be used to engineer the nucleotide sequences. For example, oligonucleotide-mediated site-directed mutagenesis may be used to introduce mutations that create new restriction sites, alter glycosylation patterns, change codon preference, produce splice variants, and so forth.

In another embodiment, sequences encoding MACP may be synthesized, in whole or in part, using chemical methods well known in the art. (See, e.g., Caruthers, M. H. et al. (1980) Nucl. Acids Res. Symp. Ser. 215-223, and Horn, T. et al. (1980) Nucl. Acids Res. Symp. Ser. 225-232.) Alternatively, MACP itself or a fragment thereof may be synthesized using chemical methods. For example, peptide synthesis can be performed using various solid-phase techniques. (See, e.g., Roberge, J. Y. et al. (1995) Science 269:202-204.) Automated synthesis may be achieved using the ABI 431A Peptide Synthesizer (The Perkin-Elmer Corp., Norwalk, Conn.). Additionally, the amino acid sequence of MACP, or any part thereof, may be altered during direct synthesis and/or combined with sequences from other proteins, or any part thereof, to produce a variant polypeptide.

The peptide may be substantially purified by preparative high performance liquid chromatography. (See, e.g., Chiez, R. M. and F. Z. Regnier (1990) Methods Enzymol. 182:392-421.) The composition of the synthetic peptides may be confirmed by amino acid analysis or by sequencing. (See, e.g., Creighton, T. (1984) Proteins, Structures and Molecular Properties, WH Freeman and Co., New York, N.Y.)

In order to express a biologically active MACP, the nucleotide sequences encoding MACP or derivatives thereof may be inserted into an appropriate expression vector, i.e., a vector which contains the necessary elements for transcriptional and translational control of the inserted coding sequence in a suitable host. These elements include regulatory sequences, such as enhancers, constitutive and inducible promoters, and 5' and 3' untranslated regions in the vector and in polynucleotide sequences encoding MACP. Such elements may vary in their strength and specificity. Specific initiation signals may also be used to achieve more efficient translation of sequences encoding MACP. Such signals include the ATG initiation codon and adjacent sequences, e.g. the Kozak sequence. In cases where sequences encoding MACP and its initiation codon and upstream regulatory sequences are inserted into the appropriate expression vector, no additional transcriptional or translational control signals may be needed. However, in cases where only coding sequence, or a fragment thereof, is inserted, exogenous translational control signals including an in-frame ATG initiation codon should be provided by the vector. Exogenous translational elements and initiation codons may be of various origins, both natural and synthetic. The efficiency of expression may be enhanced by the inclusion of enhancers appropriate for the particular host cell system used. (See, e.g., Scharf, D. et al. (1994) Results Probl. Cell Differ. 20:125-162.)

Methods which are well known to those skilled in the art may be used to construct expression vectors containing sequences encoding MACP and appropriate transcriptional and translational control elements. These methods include in vitro recombinant DNA techniques, synthetic techniques, and in vivo genetic recombination. (See, e.g., Sambrook. J. et al. (1989) Molecular Cloning, A Laboratory Manual, Cold Spring Harbor Press, Plainview, N.Y. ch. 4, 8, and 16-17; and Ausubel, F. M. et al. (1995, and periodic supplements) Current Protocols in Molecular Biology, John Wiley & Sons, New York, N.Y. ch. 9, 13, and 16.)

A variety of expression vector/host systems may be utilized to contain and express sequences encoding MACP. These include, but are not limited to, microorganisms such as bacteria transformed with recombinant bacteriophage, plasmid, or cosmid DNA expression vectors; yeast transformed with yeast expression vectors; insect cell systems infected with viral expression vectors (e.g., baculovirus); plant cell systems transformed with viral expression vectors (e.g., cauliflower mosaic virus (CaMV) or tobacco mosaic virus (TMV)) or with bacterial expression vectors (e.g., Ti or pBR322 plasmids); or animal cell systems. The invention is not limited by the host cell employed.

In bacterial systems, a number of cloning and expression vectors may be selected depending upon the use intended for polynucleotide sequences encoding MACP. For example, routine cloning, subcloning, and propagation of polynucleotide sequences encoding MACP can be achieved using a multifunctional E. coli vector such as Bluescript® (Stratagene) or pSport1™ plasmid (GIBCO BRL). Ligation of sequences encoding MACP into the vector's multiple cloning site disrupts the lacZ gene, allowing a colorimetric screening procedure for identification of transformed bacteria containing recombinant molecules. In addition, these vectors may be useful for in vitro transcription, dideoxy sequencing, single strand rescue with helper phage, and creation of nested deletions in the cloned sequence. (See, e.g., Van Heeke, G. and S. M. Schuster (1989) J. Biol. Chem. 264:5503-5509.) When large quantities of MACP are needed, e.g. for the production of antibodies, vectors which direct high level expression of MACP may be used. For example, vectors containing the strong, inducible T5 or T7 bacteriophage promoter may be used.

Yeast expression systems may be used for production of MACP. A number of vectors containing constitutive or inducible promoters, such as alpha factor, alcohol oxidase, and PGH, may be used in the yeast Saccharomyces cerevisiae or Pichia pastoris. In addition, such vectors direct either the secretion or intracellular retention of expressed proteins and enable integration of foreign sequences into the host genome for stable propagation. (See, e.g., Ausubel, supra; and Grant et al. (1987) Methods Enzymol. 153:516-54; Scorer, C. A. et al. (1994) Bio/Technology 12:181-184.)

Plant systems may also be used for expression of MACP. Transcription of sequences encoding MACP may be driven viral promoters, e.g., the 35S and 19S promoters of CaMV used alone or in combination with the omega leader sequence from TMV. (Takamatsu, N. (1987) EMBO J. 6:307-311.) Alternatively, plant promoters such as the small subunit of RUBISCO or heat shock promoters may be used. (See, e.g., Coruzzi, G. et al. (1984) EMBO J. 3:1671-1680;

Broglie, R. et al. (1984) Science 224:838-843; and Winter, J. et al. (1991) Results Probl. Cell Differ. 17:85-105.) These constructs can be introduced into plant cells by direct DNA transformation or pathogen-mediated transfection. (See, e.g. Hobbs, S. or Murry, L. E. in *McGraw Hill Yearbook of Science and Technology* (1992) McGraw Hill, New York, N.Y.; pp. 191-196.)

In mammalian cells, a number of viral-based expression systems may be utilized. In cases where an adenovirus is used as an expression vector, sequences encoding MACP may be ligated into an adenovirus transcription/translation complex consisting of the late promoter and tripartite leader sequence. Insertion in a non-essential E1 or E3 region of the viral genome may be used to obtain infective virus which expresses MACP in host cells. (See, e.g., Logan, J. and T. Shenk (1984) Proc. Natl. Acad. Sci. 81:3655-3659.) In addition, transcription enhancers, such as the Rous sarcoma virus (RSV) enhancer, may be used to increase expression in mammalian host cells. SV40 or EBV-based vectors may also be used for high-level protein expression.

Human artificial chromosomes (HACs) may also be employed to deliver larger fragments of DNA than can be contained in and expressed from a plasmid. HACs of about 6 kb to 10 Mb are constructed and delivered via conventional delivery methods (liposomes, polycationic amino polymers, or vesicles) for therapeutic purposes.

For long term production of recombinant proteins in mammalian systems, stable expression of MACP in cell lines is preferred. For example, sequences encoding MACP can be transformed into cell lines using expression vectors which may contain viral origins of replication and/or endogenous expression elements and a selectable marker gene on the same or on a separate vector. Following the introduction of the vector, cells may be allowed to grow for about 1 to 2 days in enriched media before being switched to selective media. The purpose of the selectable marker is to confer resistance to a selective agent, and its presence allows growth and recovery of cells which successfully express the introduced sequences. Resistant clones of stably transformed cells may be propagated using tissue culture techniques appropriate to the cell type.

Any number of selection systems may be used to recover transformed cell lines. These include, but are not limited to, the herpes simplex virus thymidine kinase and adenine phosphoribosyltransferase genes, for use in tk or apr cells, respectively. (See, e.g., Wigler. M. et al. (1977) Cell 11:223-232; and Lowy, I. et al. (1980) Cell 22:817-823.) Also, antimetabolite, antibiotic, or herbicide resistance can be used as the basis for selection. For example, dhfr confers resistance to methotrexate; neo confers resistance to the aminoglycosides neomycin and G-418; and als or pat confer resistance to chlorsulfuron and phosphinotricin acetyltransferase, respectively. (See, e.g., Wigler, M. et al. (1980) Proc. Natl. Acad. Sci. 77:3567-3570; Colbere-Garapin, F. et al (1981) J. Mol. Biol. 150:1-14; and Murry, supra.) Additional selectable genes have been described, e.g., trpB and hisD, which alter cellular requirements for metabolites. (See, e.g., Hartman, S. C. and R. C. Mulligan (1988) Proc. Natl. Acad. Sci. 85:8047-8051.) Visible markers, e.g., anthocyanins, green fluorescent proteins (GFP) (Clontech, Palo Alto, Calif.), β glucuronidase and its substrate β-D-glucuronoside, or luciferase and its substrate luciferin may be used. These markers can be used not only to identify transformants, but also to quantify the amount of transient or stable protein expression attributable to a specific vector system. (See, e.g., Rhodes, C. A. et al. (1995) Methods Mol. Biol. 55:121-131.)

Although the presence/absence of marker gene expression suggests that the gene of interest is also present, the presence and expression of the gene may need to be confirmed. For example, if the sequence encoding MACP is inserted within a marker gene sequence, transformed cells containing sequences encoding MACP can be identified by the absence of marker gene function. Alternatively, a marker gene can be placed in tandem with a sequence encoding MACP under the control of a single promoter. Expression of the marker gene in response to induction or selection usually indicates expression of the tandem gene as well.

In general, host cells that contain the nucleic acid sequence encoding MACP and that express MACP may be identified by a variety of procedures known to those of skill in the art. These procedures include, but are not limited to, DNA-DNA or DNA-RNA hybridizations, PCR amplification, and protein bioassay or immunoassay techniques which include membrane, solution, or chip based technologies for the detection and/or quantification of nucleic acid or protein sequences.

Immunological methods for detecting and measuring the expression of MACP using either specific polyclonal or monoclonal antibodies are known in the art. Examples of such techniques include enzyme-linked immunosorbent assays (ELISAs), radioimmunoassays (RIAs), and fluorescence activated cell sorting (FACS). A two-site, monoclonal-based immunoassay utilizing monoclonal antibodies reactive to two non-interfering epitopes on MACP is preferred, but a competitive binding assay may be employed. These and other assays are well known in the art. (See, e.g., Hampton, R. et al. (1990) *Serological Methods, a Laboratory Manual*, APS Press, St Paul, Minn., Section IV; Coligan, J. E. et al. (1997 and periodic supplements) *Current Protocols in Immunology*, Greene Pub. Associates and Wiley-Interscience, New York, N.Y.; and Maddox, D. E. et al. (1983) J. Exp. Med. 158:1211-1216).

A wide variety of labels and conjugation techniques are known by those skilled in the art and may be used in various nucleic acid and amino acid assays. Means for producing labeled hybridization or PCR probes for detecting sequences related to polynucleotides encoding MACP include oligolabeling, nick translation, end-labeling, or PCR amplification using a labeled nucleotide. Alternatively, the sequences encoding MACP, or any fragments thereof, may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits, such as those provided by Pharmacia & Upjohn (Kalamazoo, Mich.), Promega (Madison, Wis.), and U.S. Biochemical Corp. (Cleveland, Ohio). Suitable reporter molecules or labels which may be used for ease of detection include radionuclides, enzymes, fluorescent, chemiluminescent, or chromogenic agents, as well as substrates, cofactors, inhibitors, magnetic particles, and the like.

Host cells transformed with nucleotide sequences encoding MACP may be cultured under conditions suitable for the expression and recovery of the protein from cell culture. The protein produced by a transformed cell may be secreted or retained intracellularly depending on the sequence and/or the vector used. As will be understood by those of skill in the art, expression vectors containing polynucleotides which encode MACP may be designed to contain signal sequences which direct secretion of MACP through a prokaryotic or eukaryotic cell membrane.

In addition, a host cell strain may be chosen for its ability to modulate expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to specify protein targeting, folding, and/or activity. Different host cells which have specific cellular machinery and characteristic mechanisms for post-translational activities (e.g., CHO, HeLa, MDCK, HEK293, and WI38), are available from the American Type Culture Collection (ATCC. Bethesda, Md.) and may be chosen to ensure the correct modification and processing of the foreign protein.

In another embodiment of the invention, natural, modified, or recombinant nucleic acid sequences encoding MACP may be ligated to a heterologous sequence resulting in translation of a fusion protein in any of the aforementioned host systems. For example, a chimeric MACP protein containing a heterologous moiety that can be recognized by a commercially available antibody may facilitate the screening of peptide libraries for inhibitors of MACP activity. Heterologous protein and peptide moieties may also facilitate purification of fusion proteins using commercially available affinity matrices. Such moieties include, but are not limited to, glutathione S-transferase (GST), maltose binding protein (MBP), thioredoxin (Trx), calmodulin binding peptide (CBP), 6-His, FLAG, c-myc, and hemagglutinin (HA). GST, MBP, Trx, CBP, and 6-His enable purification of their cognate fusion proteins on immobilized glutathione, maltose, phenylarsine oxide, calmodulin, and metal-chelate resins, respectively. FLAG, c-myc, and hemagglutinin (HA) enable immunoaffinity purification of fusion proteins using commercially available monoclonal and polyclonal antibodies that specifically recognize these epitope tags. A fusion protein may also be engineered to contain a proteolytic cleavage site located between the MACP encoding sequence and the heterologous protein sequence, so that MACP may be cleaved away from the heterologous moiety following purification. Methods for fusion protein expression and purification are discussed in Ausubel, F. M. et al. (1995 and periodic supplements) *Current Protocols in Molecular Biology*, John Wiley & Sons, New York, N.Y., ch 10. A variety of commercially available kits may also be used to facilitate expression and purification of fusion proteins.

In a further embodiment of the invention, synthesis of radiolabeled MACP may be achieved in vitro using the TNT™ rabbit reticulocyte lysate or wheat germ extract systems (Promega, Madison, Wis.). These systems couple transcription and translation of protein-coding sequences operably associated with the T7, T3, or SP6 promoters. Translation takes place in the presence of a radiolabeled amino acid precursor, preferably $^{35}$S-methionine.

Fragments of MACP may be produced not only by recombinant production, but also by direct peptide synthesis using solid-phase techniques. (See, e.g., Creighton, supra pp. 55-60.) Protein synthesis may be performed by manual techniques or by automation. Automated synthesis may be achieved, for example, using the Applied Biosystems 431A Peptide Synthesizer (The Perkin-Elmer Corp., Norwalk, Conn.). Various fragments of MACP may be synthesized separately and then combined to produce the full length molecule.

Therapeutics

Partial chemical and structural similarity, e.g., in the context of sequences and motifs, exists between regions of MACP and various known molecules associated with cell proliferation. In addition, the expression of MACP is closely associated with cell proliferation and the immune response. Therefore, MACP appears to play a role in cell proliferative and immune disorders. Further, in cell proliferative disorders associated with increased expression or activity of MACP, it is desirable to decrease the expression of MACP. In immune disorders or cell proliferative disorders associated with a decrease in expression or activity of MACP, it is desirable to provide the protein or to increase the expression of MACP.

In one embodiment. MACP or a fragment or derivative thereof may be administered to a subject to treat or prevent a cell proliferative disorder associated with a decrease in expression or activity of MACP. Such a cell proliferative disorder may include, but is not limited to actinic keratosis, arteriosclerosis, atherosclerosis, bursitis, cirrhosis, hepatitis, mixed connective tissue disease (MCTD), myelofibrosis, paroxysmal nocturnal hemoglobinuria, polycythemia vera, psoriasis, primary thrombocythemia, and cancers including adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus.

In another embodiment, a pharmaceutical composition comprising purified MACP may be used to treat or prevent a cell proliferative disorder including, but not limited to, those listed above.

In another embodiment, an agonist which is specific for MACP may be administered to a subject to treat or prevent a cell proliferative disorder including, but not limited to, those listed above.

In another further embodiment, a vector capable of expressing MACP, or a fragment or a derivative thereof, may be administered to a subject to treat or prevent a cell proliferative disorder including, but not limited to, those listed above.

In a further embodiment, antagonists which decrease the expression or activity of MACP may be administered to a subject to treat or prevent a cell proliferative disorder associated with an increase in expression or activity of MACP. Such cell proliferative disorders include, but are not limited to, those listed above. In one aspect, antibodies which specifically bind MACP may be used directly as an antagonist or indirectly as a targeting or delivery mechanism for bringing a pharmaceutical agent to cells or tissue which express MACP.

In another embodiment, a vector expressing the complement of the polynucleotide encoding MACP may be administered to a subject to treat or prevent a cell proliferative disorder including, but not limited to, those listed above.

In another embodiment, MACP or a fragment or derivative thereof may be administered to a subject to treat or prevent an immune disorder. Such a disorder may include, but is not limited to, acquired immunodeficiency syndrome (AIDS), Addison's disease, adult respiratory distress syndrome, allergies, ankylosing spondylitis, amyloidosis, anemia asthma, atherosclerosis, autoimmune hemolytic anemia, autoimmune thyroiditis, bronchitis, cholecystitis, contact dermatitis. Crohn's disease, atopic dermatitis, dermatomyositis, diabetes mellitus, emphysema, episodic lymphopenia with lymphocytotoxins, erythroblastosis fetalis, erythema nodosum, atrophic gastritis, glomerulonephritis, Goodpasture's syndrome, gout, Graves' disease, Hashimoto's thyroiditis, hypereosinophilia, irritable bowel syndrome, multiple sclerosis, myasthenia gravis, myocardial or pericardial inflammation, osteoarthritis, osteoporosis, pancreatitis, polymyositis, psoriasis, Reiter's syndrome, rheumatoid arthritis, scleroderma, Sjögren's syndrome, systemic anaphylaxis, systemic lupus erythematosus, systemic sclerosis, thrombocytopenic purpura, ulcerative colitis, uveitis, Werner syndrome, complications of cancer, hemodialysis, and extracorporeal circulation, viral, bacterial, fungal, parasitic, protozoal, and helminthic infections, and trauma.

In another embodiment, a pharmaceutical composition comprising purified MACP may be used to treat or prevent an immune disorder including, but not limited to, those listed above.

In another embodiment, an agonist which is specific for MACP may be administered to a subject to treat or prevent an immune disorder including, but not limited to, those listed above.

In another further embodiment, a vector capable of expressing MACP, or a fragment or a derivative thereof, may be administered to a subject to treat or prevent an immune disorder including, but not limited to, those listed above.

In other embodiments, any of the proteins, antagonists, antibodies, agonists, complementary sequences, or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

An antagonist of MACP may be produced using methods which are generally known in the art. In particular, purified MACP may be used to produce antibodies or to screen libraries of pharmaceutical agents to identify those which specifically bind MACP. Antibodies to MACP may also be generated using methods that are well known in the art. Such antibodies may include, but are not limited to, polyclonal, monoclonal, chimeric, and single chain antibodies, Fab fragments, and fragments produced by a Fab expression library. Neutralizing antibodies (i.e., those which inhibit dimer formation) are especially preferred for therapeutic use.

For the production of polyclonal antibodies, various hosts including goats, rabbits, rats, mice, humans, and others may be immunized by injection with MACP or with any fragment or oligopeptide thereof which has immunogenic properties. Rats and mice are preferred hosts for downstream applications involving monoclonal antibody production. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, KLH, and dinitrophenol. Among adjuvants used in humans, BCG (bacilli Calmette-Guerin) and *Corynebacterium parvum* are especially preferable. (For review of methods for antibody production and analysis, see, e.g., Harlow, E. and Lane, D. (1988) *Antibodies: A Laboratory Manual*, Cold Spring Harbor Laboratory, Cold Spring Harbor, N.Y.)

It is preferred that the oligopeptides, peptides, or fragments used to induce antibodies to MACP have an amino acid sequence consisting of at least about 5 amino acids, and, more preferably, of at least about 14 amino acids. It is also preferable that these oligopeptides, peptides, or fragments are identical to a portion of the amino acid sequence of the natural protein and contain the entire amino acid sequence of a small, naturally occurring molecule. Short stretches of MACP amino acids may be fused with those of another protein, such as KLH, and antibodies to the chimeric molecule may be produced.

Monoclonal antibodies to MACP may be prepared using any technique which provides for the production of antibody molecules by continuous cell lines in culture. These include, but are not limited to, the hybridoma technique, the human B-cell hybridoma technique, and the EBV-hybridoma technique. (See, e.g., Kohler, G. et al. (1975) Nature 256:495-497; Kozbor, D. et al. (1985) J. Immunol. Methods 81:31-42; Cote, R. J. et al. (1983) Proc. Natl. Acad. Sci. 80:2026-2030; and Cole, S. P. et al. (1984) Mol. Cell Biol. 62:109-120.)

In addition, techniques developed for the production of "chimeric antibodies," such as the splicing of mouse antibody genes to human antibody genes to obtain a molecule with appropriate antigen specificity and biological activity, can be used. (See, e.g., Morrison, S. L. et al. (1984) Proc. Natl. Acad. Sci. 81:6851-6855; Neuberger, M. S. et al. (1984) Nature 312:604-608; and Takeda, S. et al. (1985) Nature 314:452-454.) Alternatively, techniques described for the production of single chain antibodies may be adapted, using methods known in the art, to produce MACP-specific single chain antibodies. Antibodies with related specificity, but of distinct idiotypic composition, may be generated by chain shuffling from random combinatorial immunoglobulin libraries. (See, e.g., Burton D. R. (1991) Proc. Natl. Acad. Sci. 88:10134-10137.)

Antibodies may also be produced by inducing in vivo production in the lymphocyte population or by screening immunoglobulin libraries or panels of highly specific binding reagents as disclosed in the literature. (See, e.g., Orlandi, R. et al. (1989) Proc. Natl. Acad. Sci. 86: 3833-3837; and Winter, G. et al. (1991) Nature 349:293-299.)

Antibody fragments which contain specific binding sites for MACP may also be generated. For example, such fragments include, but are not limited to, F(ab')2 fragments produced by pepsin digestion of the antibody molecule and Fab fragments generated by reducing the disulfide bridges of the F(ab')2 fragments. Alternatively, Fab expression libraries may be constructed to allow rapid and easy identification or monoclonal Fab fragments with the desired specificity. (See, e.g., Huse. W. D. et al. (1989) Science 246:1275-1281.)

Various immunoassays may be used for screening to identify antibodies having the desired specificity and minimal cross-reactivity. Numerous protocols for competitive binding or immunoradiometric assays using either polyclonal or monoclonal antibodies with established specificities are well known in the art. Such immunoassays typically involve the measurement of complex formation between MACP and its specific antibody. A two-site, monoclonal-based immunoassay utilizing monoclonal antibodies reactive to two non-interfering MACP epitopes is preferred, but a competitive binding assay may also be employed. (Maddox, supra.)

Various methods such as Scatchard analysis in conjunction with radioimmunoassay techniques may be used to assess the affinity of antibodies for MACP. Affinity is expressed as an association constant, $K_a$, which is defined as the molar concentration of MACP-antibody complex divided by the molar concentrations of free antigen and free antibody under equilibrium conditions. The $K_a$ determined for a preparation of polyclonal antibodies, which are heterogeneous in their affinities for multiple MACP epitopes, represents the average affinity, or avidity, of the antibodies for MACP. The $K_a$ determined for a preparation of monoclonal antibodies, which are monospecific for a particular MACP epitope, represents a true measure of affinity. High-affinity antibody preparations with $K_a$ ranging from about $10^9$ to $10^{12}$ L/mole are preferred for use in immunoassays in which the MACP-antibody complex must withstand rigorous manipulations. Low-affinity antibody preparations with $K_a$ ranging from about $10^6$ to $10^7$ L/mole are preferred for use in immunopurification and similar procedures which ultimately require dissociation of MACP, preferably in active form, from the antibody. (Catty, D. (1988) *Antibodies, Volume 1: A Practical Approach*, IRL Press, Washington, D.C.; and Liddell, J. E. and Cryer, A. (1991) *A Practical Guide to Monoclonal Antibodies*, John Wiley & Sons, New York, N.Y.)

The titre and avidity of polyclonal antibody preparations may be further evaluated to determine the quality and suitability of such preparations for certain downstream applications. For example, a polyclonal antibody preparation containing at least 1-2 mg specific antibody/ml, preferably 5-10 mg specific antibody/ml, is preferred for use in procedures requiring precipitation of MACP-antibody complexes. Procedures for evaluating antibody specificity, titer, and avidity, and guidelines for antibody quality and usage in various applications, are generally available. (See, e.g., Catty, Supra, and Coligan et al. Supra.)

In another embodiment of the invention, the polynucleotides encoding MACP, or any fragment or complement thereof, may be used for therapeutic purposes. In one aspect, the complement of the polynucleotide encoding MACP may be used in situations in which it would be desirable to block the transcription of the mRNA. In particular, cells may be transformed with sequences complementary to polynucleotides encoding MACP. Thus, complementary molecules or fragments may be used to modulate MACP activity, or to achieve regulation of gene function. Such technology is now well known in the art, and sense or antisense oligonucleotides or larger fragments can be designed from various locations along the coding or control regions of sequences encoding MACP.

Expression vectors derived from retroviruses, adenoviruses, or herpes or vaccinia viruses, or from various bacterial plasmids, may be used for delivery of nucleotide sequences to the targeted organ, tissue, or cell population. Methods which are well known to those skilled in the art can be used to construct vectors to express nucleic acid sequences complementary to the polynucleotides encoding MACP. (See, e.g., Sambrook, supra; and Ausubel, supra.)

Genes encoding MACP can be turned off by transforming a cell or tissue with expression vectors which express high levels of a polynucleotide, or fragment thereof, encoding MACP. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector, and may last even longer if appropriate replication elements are part of the vector system.

As mentioned above, modifications of gene expression can be obtained by designing complementary sequences or antisense molecules (DNA, RNA, or PNA) to the control, 5', or regulatory regions of the gene encoding MACP. Oligonucleotides derived from the transcription initiation site, e.g., between about positions –10 and +10 from the start site, are preferred. Similarly, inhibition can be achieved using triple helix base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature. (See, e.g., Gee, J. E. et al. (1994) in Huber, B. E. and B. I. Carr, *Molecular and Immunologic Approaches*, Futura Publishing Co., Mt. Kisco, N.Y., pp. 163-177.) A complementary sequence or antisense molecule may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. For example, engineered hammerhead motif ribozyme molecules may specifically and efficiently catalyze endonucleolytic cleavage of sequences encoding MACP.

Specific ribozyme cleavage sites within any potential RNA target are initially identified by scanning the target molecule for ribozyme cleavage sites, including the following sequences: GUA, GUU, and GUC. Once identified, short RNA sequences of between 15 and 20 ribonucleotides, corresponding to the region of the target gene containing the cleavage site, may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding MACP. Such DNA sequences may be incorporated into a wide variety of vectors with suitable RNA polymerase promoters such as T7 or SP6. Alternatively, these cDNA constructs that synthesize complementary RNA, constitutively or inducibly, can be introduced into cell lines, cells, or tissues.

RNA molecules may be modified to increase intracellular stability and half-life. Possible modifications include, but are not limited to, the addition of flanking sequences at the 5' and/or 3' ends of the molecule, or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections, or by polycationic amino polymers may be achieved using methods which are well known in the art. (See, e.g., Goldman, C. K. et al. (1997) *Nature Biotechnology* 15:462-466.) Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical or sterile composition, in conjunction with a pharmaceutically acceptable carrier, for any of the therapeutic effects discussed above. Such pharmaceutical compositions may consist of MACP, antibodies to MACP, and mimetics, agonists, antagonists, or inhibitors of MACP. The compositions may be administered alone or in combination with at least one other agent, such as a stabilizing compound, which may be administered in any sterile, biocompatible pharmaceutical carrier including, but not limited to, saline, buffered saline, dextrose, and water. The compositions may be administered to a patient alone, or in combination with other agents, drugs, or hormones.

The pharmaceutical compositions utilized in this invention may be administered by any number of routes including, but not limited to, oral, intravenous, intramuscular, intra-arterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combining active compounds with solid excipient and processing the resultant mixture of granules (optionally, after grinding) to obtain tablets or dragee cores. Suitable auxiliaries can be added, if desired. Suitable excipients include carbohydrate or protein fillers, such as sugars, including lactose, sucrose, mannitol, and sorbitol; starch from corn, wheat, rice, potato, or other plants; cellulose, such as methyl cellulose, hydroxypropylmethyl-cellulose, or sodium carboxymethylcellulose; gums, including arabic and tragacanth; and proteins, such as gelatin and collagen. If desired, disintegrating or solubilizing agents may be added, such as the cross-linked polyvinyl pyrrolidone, agar, and alginic acid or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e. dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with fillers or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils, such as sesame oil, or synthetic fatty acid esters, such as ethyl oleate, triglycerides, or liposomes. Non-lipid polycationic amino polymers may also be used for delivery. Optionally, the suspension may also contain suitable stabilizers or agents to increase the solubility of the compounds and allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to hydrochloric, sulfuric, acetic, lactic, tartaric, malic, and succinic acid. Salts tend to be more soluble in aqueous or other protonic solvents than are the corresponding free base forms. In other cases, the preferred preparation may be a lyophilized powder which may contain any or all of the following: 1 mM to 50 mM histidine, 0.1% to 2% sucrose, and 2% to 7% mannitol, at a pH range of 4.5 to 5.5, that is combined with buffer prior to use.

After pharmaceutical compositions have been prepared, they can be placed in an appropriate container and labeled for treatment of an indicated condition. For administration of MACP, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells or in animal models such as mice, rats, rabbits, dogs, or pigs. An animal model may also be used to determine the appropriate concentration range and route of administration. Such information can then be used to determine useful doses and routes for administration in humans.

A therapeutically effective dose refers to that amount of active ingredient, for example MACP or fragments thereof, antibodies of MACP, and agonists, antagonists or inhibitors of MACP, which ameliorates the symptoms or condition. Therapeutic efficacy and toxicity may be determined by standard pharmaceutical procedures in cell cultures or with experimental animals, such as by calculating the $ED_{50}$ (the dose therapeutically effective in 50% of the population) or $LD_{50}$ (the dose lethal to 50% of the population) statistics. The dose ratio of therapeutic to toxic effects is the therapeutic index, and it can be expressed as the $ED_{50}/LD_{50}$ ratio. Pharmaceutical compositions which exhibit large therapeutic indices are preferred. The data obtained from cell culture assays and animal studies are used to formulate a range of dosage for human use. The dosage contained in such compositions is preferably within a range of circulating concentrations that includes the $ED_{50}$ with little or no toxicity. The dosage varies within this range depending upon the dosage form employed, the sensitivity of the patient, and the route of administration.

The exact dosage will be determined by the practitioner, in light of factors related to the subject requiring treatment. Dosage and administration are adjusted to provide sufficient levels of the active moiety or to maintain the desired effect. Factors which may be taken into account include the severity of the disease state, the general health of the subject, the age, weight, and gender of the subject, time and frequency of administration, drug combination(s), reaction sensitivities, and response to therapy. Long-acting pharmaceutical compositions may be administered every 3 to 4 days, every week, or biweekly depending on the half-life and clearance rate of the particular formulation.

Normal dosage amounts may vary from about 0.1 µg to 100,000 µg, up to a total dose of about 1 gram, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

Diagnostics

In another embodiment, antibodies which specifically bind MACP may be used for the diagnosis of disorders characterized by expression of MACP, or in assays to monitor patients being treated with MACP or agonists, antagonists, or inhibitors of MACP. Antibodies useful for diagnostic purposes may be prepared in the same manner as described above for therapeutics. Diagnostic assays for MACP include methods which utilize the antibody and a label to detect MACP in human body fluids or in extracts of cells or tissues. The antibodies may be used with or without modification, and may be labeled by covalent or non-covalent attachment of a reporter molecule. A wide variety of reporter molecules, several of which are described above, are known in the art and may be used.

A variety of protocols for measuring MACP, including ELISAs, RIAs, and FACS, are known in the art and provide a basis for diagnosing altered or abnormal levels of MACP expression. Normal or standard values for MACP expression are established by combining body fluids or cell extracts taken from normal mammalian subjects, preferably human, with antibody to MACP under conditions suitable for complex formation. The amount of standard complex formation may be quantitated by various methods, preferably by photometric means. Quantities of MACP expressed in subject, control, and disease samples from biopsied tissues are compared with the standard values. Deviation between standard and subject values establishes the parameters for diagnosing disease.

In another embodiment of the invention, the polynucleotides encoding MACP may be used for diagnostic purposes. The polynucleotides which may be used include oligonucleotide sequences, complementary RNA and DNA molecules, and PNAs. The polynucleotides may be used to detect and quantitate gene expression in biopsied tissues in which expression of MACP may be correlated with disease. The diagnostic assay may be used to determine absence, presence, and excess expression of MACP, and to monitor regulation of MACP levels during therapeutic intervention.

In one aspect, hybridization with PCR probes which are capable of detecting polynucleotide sequences, including genomic sequences, encoding MACP or closely related molecules may be used to identify nucleic acid sequences which encode MACP. The specificity of the probe, whether it is made from a highly specific region, e.g., the 5' regulatory region, or from a less specific region, e.g. a conserved motif, and the stringency of the hybridization or amplification (maximal, high, intermediate, or low), will determine whether the probe identifies only naturally occurring sequences encoding MACP, allelic variants, or related sequences.

Probes may also be used for the detection of related sequences, and should preferably have at least 50% sequence identity to any of the MACP encoding sequences. The hybridization probes of the subject invention may be DNA or RNA and may be derived from the sequence of SEQ ID NO:6, SEQ ID NO:7. SEQ ID NO:8. SEQ ID NO:9. SEQ ID NO:10, or from genomic sequences including promoters, enhancers, and introns of the MACP gene.

Means for producing specific hybridization probes for DNAs encoding MACP include the cloning of polynucleotide sequences encoding MACP or MACP derivatives into vectors for the production of mRNA probes. Such vectors are known in the art, are commercially available, and may be used to synthesize RNA probes in vitro by means of the addition of the appropriate RNA polymerases and the appropriate labeled nucleotides. Hybridization probes may be labeled by a variety of reporter groups, for example, by radionuclides such as $^{32}P$ or $^{35}S$, or by enzymatic labels, such as alkaline phosphatase coupled to the probe via avidin/biotin coupling systems, and the like.

Polynucleotide sequences encoding MACP may be used for the diagnosis of a disorder associated with expression of MACP. Examples of such a disorder include, but are not limited to, cell proliferative disorders such as actinic keratosis, arteriosclerosis, atherosclerosis, bursitis, cirrhosis, hepatitis, mixed connective tissue disease (MCTD), myelofibrosis, paroxysmal nocturnal hemoglobinuria, polycythemia vera, psoriasis, primary thrombocythemia, and cancers including adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; and an immune disorder such as acquired immunodeficiency syndrome (AIDS), Addison's disease, adult respiratory distress syndrome, allergies, ankylosing spondylitis, amyloidosis, anemia, asthma atherosclerosis, autoimmune hemolytic anemia, autoimmune thyroiditis, bronchitis, cholecystitis, contact dermatitis, Crohn's disease, atopic dermatitis, dermatomyositis, diabetes mellitus, emphysema, episodic lymphopenia with lymphocytotoxins, erythroblastosis fetalis, erythema nodosum, atrophic gastritis, glomerulonephritis, Goodpasture's syndrome, gout, Graves' disease, Hashimoto's thyroiditis, hypereosinophilia, irritable bowel syndrome, multiple sclerosis, myasthenia gravis, myocardial or pericardial inflammation, osteoarthritis, osteoporosis, pancreatitis, polymyositis, psoriasis, Reiter's syndrome, rheumatoid arthritis, scleroderma, Sjögren's syndrome, systemic anaphylaxis, systemic lupus erythematosus, systemic sclerosis, thrombocytopenic purpura, ulcerative colitis, uveitis, Werner syndrome, complications of cancer, hemodialysis, and extracorporeal circulation, viral, bacterial, fungal, parasitic, protozoal, and helminthic infections, and trauma. The polynucleotide sequences encoding MACP may be used in Southern or Northern analysis, dot blot, or other membrane-based technologies; in PCR technologies; in dipstick, pin, and ELISA assays; and in microarrays utilizing fluids or tissues from patients to detect altered MACP expression. Such qualitative or quantitative methods are well known in the art.

In a particular aspect, the nucleotide sequences encoding MACP may be useful in assays that detect the presence of associated disorders, particularly those mentioned above. The nucleotide sequences encoding MACP may be labeled by standard methods and added to a fluid or tissue sample from a patient under conditions suitable for the formation of hybridization complexes. After a suitable incubation period, the sample is washed and the signal is quantitated and compared with a standard value. If the amount of signal in the patient sample is significantly altered in comparison to a control sample then the presence of altered levels of nucleotide sequences encoding MACP in the sample indicates the presence of the associated disorder. Such assays may also be used to evaluate the efficacy of a particular therapeutic treatment regimen in animal studies, in clinical trials, or to monitor the treatment of an individual patient.

In order to provide a basis for the diagnosis of a disorder associated with expression of MACP, a normal or standard profile for expression is established. This may be accomplished by combining body fluids or cell extracts taken from normal subjects, either animal or human, with a sequence, or a fragment thereof, encoding MACP, under conditions suitable for hybridization or amplification. Standard hybridization may be quantified by comparing the values obtained from normal subjects with values from an experiment in which a known amount of a substantially purified polynucleotide is used. Standard values obtained in this manner may be compared with values obtained from samples from patients who are symptomatic for a disorder. Deviation from standard values is used to establish the presence of a disorder.

Once the presence of a disorder is established and a treatment protocol is initiated, hybridization assays may be repeated on a regular basis to determine if the level of expression in the patient begins to approximate that which is observed in the normal subject. The results obtained from successive assays may be used to show the efficacy of treatment over a period ranging from several days to months.

With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding MACP may involve the use of PCR. These oligomers may be chemically synthesized, generated enzymatically, or produced in vitro. Oligomers will preferably contain a fragment of a polynucleotide encoding MACP, or a fragment of a polynucleotide complementary to the polynucleotide encoding MACP, and will be employed under optimized conditions for identification of a specific gene or condition. Oligomers may also be employed under less stringent conditions for detection or quantitation of closely related DNA or RNA sequences.

Methods which may also be used to quantitate the expression of MACP include radiolabeling or biotinylating nucleotides, coamplification of a control nucleic acid, and interpolating results from standard curves. (See, e.g., Melby, P. C. et al. (1993) J. Immunol. Methods 159:235-244; and Duplaa, C. et al. (1993) Anal. Biochem. 229-236.) The speed of quantitation of multiple samples may be accelerated by running the assay in an ELISA format where the oligomer of interest is presented in various dilutions and a spectrophotometric or calorimetric response gives rapid quantitation.

In further embodiments, oligonucleotides or longer fragments derived from any of the polynucleotide sequences described herein may be used as targets in a microarray. The microarray can be used to monitor the expression level of large numbers of genes simultaneously and to identify genetic variants, mutations, and polymorphisms. This information may be used to determine gene function, to understand the genetic basis of a disorder, to diagnose a disorder, and to develop and monitor the activities of therapeutic agents.

Microarrays may be prepared, used, and analyzed using methods known in the art. (See, e.g., Brennan, T. M. et al. (1995) U.S. Pat. No. 5,474,796; Schena, M. et al. (1996) Proc. Natl. Acad. Sci. 93:10614-10619; Baldeschweiler et al. (1995) PCT application WO95/251116; Shalon, D. et al. (1995) PCT application WO95/35505; Heller, R. A. et al. (1997) Proc. Natl. Acad. Sci. 94:2150-2155; and Heller, M. J. et al. (1997) U.S. Pat. No. 5,605,662.)

In another embodiment of the invention, nucleic acid sequences encoding MACP may be used to generate hybridization probes useful in mapping the naturally occurring genomic sequence. The sequences may be mapped to a particular chromosome, to a specific region of a chromosome, or to artificial chromosome constructions, e.g., human artificial chromosomes (HACs), yeast artificial chromosomes (YACs), bacterial artificial chromosomes (BACs), bacterial P1 constructions, or single chromosome cDNA libraries. (See, e.g., Price, C. M. (1993) Blood Rev. 7:127-134; and Trask, B. J. (1991) Trends Genet. 7:149-154.)

Fluorescent in situ hybridization (FISH) may be correlated with other physical chromosome mapping techniques and genetic map data. (See, e.g., Heinz-Ulrich, et al. (1995) in Meyers, R. A. (ed.) *Molecular Biology and Biotechnology*, VCH Publishers New York, N.Y., pp. 965-968.) Examples of genetic map data can be found in various scientific journals or at the Online Mendelian Inheritance in Man (OMIM) site. Correlation between the location of the gene encoding MACP on a physical chromosomal map and a specific disorder, or a predisposition to a specific disorder, may help define the region of DNA associated with that disorder. The nucleotide sequences of the invention may be used to detect differences in gene sequences among normal, carrier, and affected individuals.

In situ hybridization of chromosomal preparations and physical mapping techniques, such as linkage analysis using established chromosomal markers, may be used for extending genetic maps. Often the placement of a gene on the chromosome of another mammalian species, such as mouse, may reveal associated markers even if the number or arm of a particular human chromosome is not known. New sequences can be assigned to chromosomal arms by physical mapping. This provides valuable information to investigators searching for disease genes using positional cloning or other gene discovery techniques. Once the disease or syndrome has been crudely localized by genetic linkage to a particular genomic region, e.g., ataxia-telangiectasia to 11q22-23, any sequences mapping to that area may represent associated or regulatory genes for further investigation. (See, e.g., Gatti, R. A. et al. (1988) Nature 336:577-580.) The nucleotide sequence of the subject invention may also be used to detect differences in the chromosomal location due to translocation, inversion, etc., among normal, carrier, or affected individuals.

In another embodiment of the invention, MACP, its catalytic or immunogenic fragments, or oligopeptides thereof can be used for screening libraries of compounds in any of a variety of drug screening techniques. The fragment employed in such screening may be free in solution, affixed to a solid support, borne on a cell surface, or located intracellularly. The formation of binding complexes between MACP and the agent being tested may be measured.

Another technique for drug screening provides for high throughput screening of compounds having suitable binding affinity to the protein of interest. (See, e.g., Geysen, et al. (1984) PCT application WO84/03564.) In this method, large numbers of different small test compounds are synthesized on a solid substrate, such as plastic pins or some other surface. The test compounds are reacted with MACP, or fragments thereof, and washed. Bound MACP is then detected by methods well known in the art. Purified MACP can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding MACP specifically compete with a test compound for binding MACP. In this manner, antibodies can be used to detect the presence of any peptide which shares one or more antigenic determinants with MACP.

In additional embodiments, the nucleotide sequences which encode MACP may be used in any molecular biology techniques that have yet to be developed, provided the new techniques rely on properties of nucleotide sequences that are currently known, including, but not limited to, such properties as the triplet genetic code and specific base pair interactions.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

The disclosures of all patents, applications, and publications mentioned above and below, in particular U.S. Ser. No. 60/093,827, are hereby expressly incorporated by reference.

EXAMPLES

I. Construction of cDNA Libraries

RNA was purchased from CLONTECH Laboratories, Inc. (Palo Alto, Calif.) or isolated from tissues described in Table 4. Some tissues were homogenized and lysed in guanidinium isothiocyanate, while others were homogenized and lysed in phenol or in a suitable mixture of denaturants, such as TRIZOL reagent (Life Technologies, Inc., Rockville, Md.), a monophasic solution of phenol and guanidine isothiocyanate. The resulting lysates were centrifuged over CsCl cushions or extracted with chloroform. RNA was precipitated from the lysates with either isopropanol or sodium acetate and ethanol, or by other routine methods.

Phenol extraction and precipitation of RNA were repeated as necessary to increase RNA purity. In some cases, RNA was treated with DNase. For most libraries, poly(A+) RNA was isolated using oligo d(T)-coupled paramagnetic particles (Promega Corp., Madison, Wis.), OLIGOTEX™ latex particles (QIAGEN Inc., Valencia, Calif.), or an OLIGOTEX™ mRNA purification kit (QIAGEN Inc. Valencia, Calif.). Alternatively, RNA was isolated directly from tissue lysates using other RNA isolation kits, e.g., the POLY(A)PURE™ mRNA purification kit (Ambion, Austin, Tex.).

In some cases, Stratapene, Inc. (La Jolla, Calif.), was provided with RNA and constructed the corresponding cDNA libraries. Otherwise, cDNA was synthesized and cDNA libraries were constructed with the UNIZAP™ vector system (Stratagene, Inc. La Jolla. CA) or SUPERSCRIPT™ plasmid system (Life Technologies, Inc., Rockville, Md.), using the recommended procedures or similar methods known in the art. (See, e.g., Ausubel, supra, 1997, units 5.1-6.6) Reverse transcription was initiated using oligo d(T) or random primers. Synthetic oligonucleotide adapters were ligated to double stranded cDNA, and the cDNA was digested with the appropriate restriction enzyme or enzymes. For most libraries, the cDNA was size-selected (300-1000 bp) using SEPHACRYL® S1000, SEPHAROSE® CL2B, or SEPHAROSE® CL4B column chromatography (Amersham Pharmacia Biotech Ltd., Uppsala, Sweden) or preparative agarose gel electrophoresis. cDNAs were ligated into compatible restriction enzyme sites of the polylinker of a suitable plasmid, e.g., pBLUESCRIPT™ (Stratagene, Inc., La Jolla, Calif.), pSPORT™ 1 (Life Technologies, Inc., Rockville, Md.), or pINCY (Incyte Pharmaceuticals, Inc., Palo Alto. CA). Recombinant plasmids were transformed into competent $E.$ $coli$ cells, e.g., the XL1-Blue, XL1-BlueMRF, or SOLR™ strains (Stratagene, Inc., La Jolla, Calif.), or DH5α™, DH10B, or ElectroMAX DH10B (Life Technologies, Inc. Rockville, Md.).

II. Isolation of cDNA Clones

Plasmids were recovered from host cells by in vivo excision, using the UNIZAP™ vector system (Stratagene, Inc., La Jolla, Calif.), or by cell lysis. Plasmids were purified using at least one of the following: a Magic or WIZARD® Minipreps DNA purification system (Promega Corp., Madison, Wis.); an AGTC® Miniprep purification kit (Edge Biosystems, Gaithersburg, Md.); the QIAWELL® 8 Plasmid, QIAWELL® 8 Plus Plasmid, or the QIAWELL® 8 Ultra Plasmid purification systems (QIAGEN Inc., Valencia, Calif.); or the R.E.A.L.™ Prep 96 plasmid kit (QIAGEN Inc., Valencia, Calif.). Following precipitation, plasmids were resuspended in 0.1 ml of distilled water and stored, with or without lyophilization, at 4° C.

Alternatively, plasmid DNA was amplified from host cell lysates using direct link PCR in a high-throughput format. (Rao, V. B. (1994) Anal. Biochem. 216:1-14). Host cell lysis and thermal cycling steps were carried out in a single reaction mixture. Samples were processed and stored in 384-well plates, and the concentration of amplified plasmid DNA was quantified fluorometrically using PICOGREEN® dye (Molecular Probes, Inc., Eugene, Oreg.) and a Fluoroskan II fluorescence scanner (Labsystems Oy, Helsinki, Finland).

III. Sequencing and Analysis

The cDNAs were prepared for sequencing using either an ABI PRISM CATALYST 800 (Perkin-Elmer Applied Biosystems, Foster City, Calif.) or a MICROLAB 2200 (Hamilton Co., Reno, Nev.) sequencing preparation system in combination with Peltier PTC-200 thermal cyclers (MJ Research, Inc., Watertown, Mass.). The cDNAs were sequenced using the ABI PRISM 373 or 377 sequencing systems and ABI protocols, base calling software, and kits (Perkin-Elmer Applied Biosystems). Alternatively, solutions and dyes from Amersham Pharmacia Biotech, Ltd. were used in place of the ABI kits. In some cases, reading frames were determined using standard methods (Ausubel, supra). Some of the cDNA sequences were selected for extension using the techniques disclosed in Example V.

The polynucleotide sequences derived from cDNA, extension, and shotgun sequencing were assembled and analyzed using a combination of software programs which utilize algorithms well known to those skilled in the art. Table 5 summarizes the software programs used, corresponding algorithms, references, and cutoff parameters used where applicable. The references cited in the third column of Table 5 are incorporated by reference herein. Sequence alignments were also analyzed and produced using MACD-NASIS PRO software (Hitachi Software Engineering Co., Ltd. San Bruno, Calif.) and the multisequence alignment program of LASERGENE software (DNASTAR Inc, Madison Wis.).

The polynucleotide sequences were validated by removing vector, linker, and polyA tail sequences and by masking ambiguous bases, using algorithms and programs based on BLAST, dynamic programming, and dinucleotide nearest neighbor analysis. The sequences were then queried against a selection of public databases such as GenBank primate, rodent, mammalian, vertebrate, and eukaryote databases, and BLOCKS to acquire annotation, using programs based on BLAST, FASTA, and BLIMPS. The sequences were assembled into full length polynucleotide sequences using programs based on Phred, Phrap, and Consed, and were screened for open reading frames using programs based on GeneMark, BLAST, and FASTA. This was followed by translation of the full length polynucleotide sequences to derive the corresponding full length amino acid sequences. These full length polynucleotide and amino acid sequences were subsequently analyzed by querying against databases such as the GenBank databases described above and SwissProt, BLOCKS, PRINTS, PFAM, and Prosite.

IV. Northern Analysis

Northern analysis is a laboratory technique used to detect the presence of a transcript of a gene and involves the hybridization of a labeled nucleotide sequence to a membrane on which RNAs from a particular cell type or tissue have been bound. (See, e.g., Sambrook, supra, ch. 7; and Ausubel, supra, ch. 4 and 16.)

Electronic northerns were produced using analogous computer techniques. These techniques apply BLAST to search for identical or related molecules in nucleotide databases such as GenBank or LIFESEQ® database (Incyte Pharmaceuticals). The sensitivity of the computer search was modified to determine the specificity of the match. The basis of the search is the product score, which is defined as:

$$\frac{\% \text{ sequence identity} \times \% \text{ maximum BLAST score}}{100}$$

The product score encompasses both the degree of similarity between two sequences and the length of the sequence match. For example, with a product score of 40, the match may have a possibility of a 1% to 2% error, in contrast, a product score of 70 indicates that the match will be exact. Similar molecules were identified by product scores between 15 and 40, although lower scores may identify related molecules.

Electronic northern analysis further involved the categorization of cDNA libraries by organ/tissue and disease. The organ/tissue categories included cardiovascular, dermatologic, developmental, endocrine, gastrointestinal, hematopoietic/immune, musculoskeletal, nervous, reproductive, and urologic. The disease categories included cancer, inflammation/trauma, fetal, neurological, and pooled. For each category, the number of libraries expressing the sequence of interest was divided by the total number of libraries across all categories. The results above were reported as a percentage distribution.

V. Extension of MACP Encoding Polynucleotides

Full length nucleic acid sequences (SEQ ID NO:6 through SEQ ID NO:10) were produced by extension of the component fragments described in Table 1, Column 5, using oligonucleotide primers based on those fragments. Primers were used to facilitate the extension of the known sequence "outward" generating amplicons containing new unknown nucleotide sequence for the region of interest. The initial primers were designed from the cDNA using OLIGO™ 4.06 (National Biosciences, Plymouth, Minn.), or another appropriate program, to be about 22 to 30 nucleotides in length, to have a GC content of about 50% or more, and to anneal to the target sequence at temperatures of about 68° C. to about 72° C. Any stretch of nucleotides which would result in hairpin structures and primer-primer dimerizations was avoided.

Selected human cDNA libraries were used to extend the sequence. If more than one extension is necessary or desired, additional sets of primers are designed to further extend the known region.

High fidelity amplification was obtained by following the instructions for the XL-PCR™ kit (The Perkin-Elmer Corp., Norwalk. CT) and thoroughly mixing the enzyme and reaction mix. PCR was performed using the PTC-200 thermal cycler (MJ Research. Inc. Watertown, Mass.), beginning with 40 pmol of each primer and the recommended concentrations of all other components of the kit, with the following parameters:

| Step 1 | 94° C. for 1 min (initial denaturation) |
| Step 2 | 65° C. for 1 min |
| Step 3 | 68° C. for 6 min |
| Step 4 | 94° C. for 15 sec |
| Step 5 | 65° C. for 1 min |
| Step 6 | 68° C. for 7 min |
| Step 7 | Repeat steps 4 through 6 for an additional 15 cycles |
| Step 8 | 94° C. for 15 sec |
| Step 9 | 65° C. for 1 min |
| Step 10 | 68° C. for 7:15 min |
| Step 11 | Repeat steps 8 through 10 for an additional 12 cycles |
| Step 12 | 72° C. for 8 min |
| Step 13 | 4° C. (and holding) |

A 5 µl to 10 µl aliquot of the reaction mixture was analyzed by electrophoresis on a low concentration (about 0.6% to 0.8%) agarose mini-gel to determine which reactions were successful in extending the sequence. Bands thought to contain the largest products were excised from the gel, purified using QIAQUICK™ (QIAGEN Inc.), and trimmed of overhangs using Klenow enzyme to facilitate religation and cloning.

After ethanol precipitation, the products were redissolved in 13 µl of ligation buffer, 1 µl T4-DNA ligase (15 units) and 1 µl T4 polynucleotide kinase were added, and the mixture was incubated at room temperature for 2 to 3 hours, or overnight at 16° C. Competent *E. coli* cells (in 40 µl of appropriate media) were transformed with 3 µl of ligation mixture and cultured in 80 µl of SOC medium. (See, e.g., Sambrook, supra, Appendix A, p. 2.) After incubation for one hour at 37° C., the *E. coli* mixture was plated on Luria Bertani (LB) agar (See, e.g., Sambrook, supra, Appendix A, p. 1) containing carbenicillin (2×carb). The following day, several colonies were randomly picked from each plate and cultured in 150 µl of liquid LB/2×carb medium placed in an individual well of an appropriate commercially-available sterile 96-well microtiter plate. The following day, 5 µl of each overnight culture was transferred into a non-sterile 96-well plate and, after dilution 1:10 with water, 5 µl from each sample was transferred into a PCR array.

For PCR amplification, 18 µl of concentrated PCR reaction mix (3.3×) containing 4 units of rTth DNA polymerase, a vector primer, and one or both of the gene specific primers used for the extension reaction were added to each well. Amplification was performed using the following conditions:

| Step 1 | 94° C. for 60 sec |
| Step 2 | 94° C. for 20 sec |
| Step 3 | 55° C. for 30 sec |
| Step 4 | 72° C. for 90 sec |
| Step 5 | Repeat steps 2 through 4 for an additional 29 cycles |
| Step 6 | 72° C. for 180 sec |
| Step 7 | 4° C. (and holding) |

Aliquots of the PCR reactions were run on agarose gels together with molecular weight markers. The sizes of the PCR products were compared to the original partial cDNAs, and appropriate clones were selected, ligated into plasmid, and sequenced.

In like manner, the nucleotide sequences of SEQ ID NO:6, SEQ ID NO:7, SEQ ID NO:8, SEQ ID NO:9, and SEQ ID NO:10, are used to obtain 5' regulatory sequences using the procedure above, oligonucleotides designed for 5' extension, and an appropriate genomic library.

VI. Labeling and Use of Individual Hybridization Probes

Hybridization probes derived from SEQ ID NO:6, SEQ ID NO:7, SEQ ID NO:8, SEQ ID NO:9, and SEQ ID NO:10 are employed to screen cDNAs, genomic DNAs, or mRNAs. Although the labeling of oligonucleotides, consisting of about 20 base pairs, is specifically described, essentially the same procedure is used with larger nucleotide fragments. Oligonucleotides are designed using state-of-the-art software such as OLIGO™ 4.06 software (National Biosciences) and labeled by combining 50 pmol of each oligomer, 250 µCi of [$\gamma$-$^{32}$P] adenosine triphosphate (Amersham, Chicago, Ill.), and T4 polynucleotide kinase (DuPont NEN®, Boston, Mass.). The labeled oligonucleotides are substantially purified using a Sephadex™ G-25 superfine size exclusion dextran bead column (Pharmacia & Upjohn, Kalamazoo, Mich.). An aliquot containing $10^7$ counts per minute of the labeled probe is used in a typical membrane-based hybridization analysis of human genomic DNA digested with one of the following endonucleases: Ase I, Bgl II, Eco RI, Pst I, XbaI, or Pvu II (DuPont NEN, Boston, Mass.).

The DNA from each digest is fractionated on a 0.7% agarose gel and transferred to nylon membranes (Nytran Plus, Schleicher & Schuell, Durham, N.H.). Hybridization is carried out for 16 hours at 40° C. To remove nonspecific signals, blots are sequentially washed at room temperature under increasingly stringent conditions up to 0.1× saline sodium citrate and 0.5% sodium dodecyl sulfate. After XOMAT AR™ film (Kodak, Rochester, N.Y.) is exposed to the blots to film for several hours, hybridization patterns are compared visually.

VII. Microarrays

A chemical coupling procedure and an ink jet device can be used to synthesize array elements on the surface of a substrate. (See, e.g., Baldeschweiler, supra.) An array analogous to a dot or slot blot may also be used to arrange and link elements to the surface of a substrate using thermal, UV, chemical, or mechanical bonding procedures. A typical array may be produced by hand or using available methods and machines and contain any appropriate number of elements. After hybridization, nonhybridized probes are removed and a scanner used to determine the levels and patterns of fluorescence. The degree of complementarity and the relative abundance of each probe which hybridizes to an element on the microarray may be assessed through analysis of the scanned images.

Full-length cDNAs, Expressed Sequence Tags (ESTs), or fragments thereof may comprise the elements of the microarray. Fragments suitable for hybridization can be selected using software well known in the art such as LASERGENE™. Full-length cDNAs, ESTs, or fragments thereof corresponding to one of the nucleotide sequences of the present invention, or selected at random from a cDNA library relevant to the present invention, are arranged on an appropriate substrate, e.g., a glass slide. The cDNA is fixed to the slide using, e.g., UV cross-linking followed by thermal and chemical treatments and subsequent drying. (See, e.g., Schena, M. et al. (1995) Science 270:467-470; and Shalon, D. et al. (1996) Genome Res. 6:639-645.) Fluorescent probes are prepared and used for hybridization to the elements on the substrate. The substrate is analyzed by procedures described above.

VIII. Complementary Polynucleotides

Sequences complementary to the MACP-encoding sequences, or any parts thereof, are used to detect, decrease, or inhibit expression of naturally occurring MACP. Although use of oligonucleotides comprising from about 15 to 30 base pairs is described, essentially the same procedure is used with smaller or with larger sequence fragments. Appropriate oligonucleotides are designed using OLIGO™ 4.06 software and the coding sequence of MACP. To inhibit transcription, a complementary oligonucleotide is designed from the most unique 5' sequence and used to prevent promoter binding to the coding sequence. To inhibit translation, a complementary oligonucleotide is designed to prevent ribosomal binding to the MACP-encoding transcript.

IX. Expression of MACP

Expression and purification of MACP is achieved using bacterial or virus-based expression systems. For expression of MACP in bacteria, cDNA is subcloned into an appropriate vector containing an antibiotic resistance gene and an inducible promoter that directs high levels of cDNA transcription. Examples of such promoters include, but are not limited to, the trp-lac (tac) hybrid promoter and the T5 or T7 bacteriophage promoter in conjunction with the lac operator regulatory element. Recombinant vectors are transformed into suitable bacterial hosts. e.g., BL21(DE3). Antibiotic resistant bacteria express MACP upon induction with isopropyl beta-D-thiogalactopyranoside (IPTG). Expression of MACP in eukaryotic cells is achieved by infecting insect or mammalian cell lines with recombinant *Autographica californica* nuclear polyhedrosis virus (AcMNPV), commonly known as baculovirus. The nonessential polyhedrin gene of baculovirus is replaced with cDNA encoding MACP by either homologous recombination or bacterial-mediated transposition involving transfer plasmid intermediates. Viral infectivity is maintained and the strong polyhedrin promoter drives high levels of cDNA transcription. Recombinant baculovirus is used to infect *Spodoptera frugiperda* (Sf9) insect cells in most cases, or human hepatocytes, in some cases. Infection of the latter requires additional genetic modifications to baculovirus. (See Engelhard, E. K. et al. (1994) Proc. Natl. Acad. Sci. USA 91:3224-3227; Sandig, V. et al. (1996) Hum. Gene Ther. 7:1937-1945.)

In most expression systems, MACP is synthesized as a fusion protein with, e.g., glutathione S-transferase (GST) or a peptide epitope tag, such as FLAG or 6-His, permitting rapid, single-step, affinity-based purification of recombinant fusion protein from crude cell lysates. GST, a 26-kilodalton enzyme from *Schistosoma japonicum*, enables the purification of fusion proteins on immobilized glutathione under conditions that maintain protein activity and antigenicity (Pharmacia, Piscataway, N.J.). Following purification, the GST moiety can be proteolytically cleaved from MACP at specifically engineered sites. FLAG, an 8-amino acid peptide, enables immunoaffinity purification using commercially available monoclonal and polyclonal anti-FLAG antibodies (Eastman Kodak, Rochester, N.Y.). 6-His, a stretch of six consecutive histidine residues, enables purification on metal-chelate resins (QIAGEN Inc, Chatsworth, Calif.). Methods for protein expression and purification are discussed in Ausubel, F. M. et al. (1995 and periodic supplements) *Current Protocols in Molecular Biology*, John Wiley & Sons, New York, N.Y., ch 10, 16. Purified MACP obtained by these methods can be used directly in the following activity assay.

X. Demonstration of MACP Activity

MACP activity is measured by its ability to transform NIH3T3 mouse fibroblast cells. cDNA encoding MACP is subcloned into an appropriate eukaryotic expression vector containing a strong promoter that drives high levels of cDNA expression. This construct is transfected into NIH3T3 cells using methods known in the art. Transfected cells are assessed for the following quantifiable properties characteristic of oncogenically transformed cells: growth in culture to high density associated with loss of contact inhibition, growth in suspension or in soft agar, lowered serum requirements, and ability to induce tumors when injected into immunodeficient mice. The activity of MACP is proportional to the extent of transformation of NIH3T3 cells relative to non-transfected controls.

XI. Functional Assays

MACP function is assessed by expressing the sequences encoding MACP at physiologically elevated levels in mammalian cell culture systems. cDNA is subcloned into a mammalian expression vector containing a strong promoter that drives high levels of cDNA expression. Vectors of choice include pCMV SPORT™ (Life Technologies. Gaithersburg, Md.) and pCR™ 3.1 (Invitrogen, Carlsbad, Calif., both of which contain the cytomegalovirus promoter. 5-10 µg of recombinant vector are transiently transfected into a human cell line, preferably of endothelial or hematopoietic origin, using either liposome formulations or electroporation. 1-2 µg of an additional plasmid containing sequences encoding a marker protein are co-transfected. Expression of a marker protein provides a means to distinguish transfected cells from nontransfected cells and is a reliable predictor of cDNA expression from the recombinant vector. Marker proteins of choice include, e.g., Green Fluorescent Protein (GFP) (Clontech, Palo Alto, Calif.), CD64, or a CD64-GFP fusion protein. Flow cytometry (FCM), an automated, laser optics-based technique, is used to identify transfected cells expressing GFP or CD64-GFP, and to evaluate properties, for example, their apoptotic state. FCM detects and quantifies the uptake of fluorescent molecules that diagnose events preceding or coincident with cell death. These events include changes in nuclear DNA content as measured by staining of DNA with propidium iodide; changes in cell size and granularity as measured by forward light scatter and 90 degree side light scatter; down-regulation of DNA synthesis as measured by decrease in bromodeoxyuridine uptake; alterations in expression of cell surface and intracellular proteins as measured by reactivity with specific antibodies; and alterations in plasma membrane composition as measured by the binding of fluorescein-conjugated Annexin V protein to the cell surface. Methods in flow cytometry are discussed in Ormerod, M. G. (1994) Flow Cytometry, Oxford, New York, N.Y.

The influence of MACP on gene expression can be assessed using highly purified populations of cells transfected with sequences encoding MACP and either CD64 or CD64-GFP. CD64 and CD64-GFP are expressed on the surface of transfected cells and bind to conserved regions of human immunoglobulin G (IgG). Transfected cells are efficiently separated from nontransfected cells using magnetic beads coated with either human IgG or antibody against CD64 (DYNAL, Lake Success, N.Y.). mRNA can be purified from the cells using methods well known by those of skill in the art. Expression of mRNA encoding MACP and other genes of interest can be analyzed by Northern analysis or microarray techniques.

XII. Production of MACP Specific Antibodies

MACP substantially purified using polyacrylamide gel electrophoresis (PAGE) (see, e.g., Harrington, M. G. (1990) Methods Enzymol. 182:488-495), or other purification techniques, is used to immunize rabbits and to produce antibodies using standard protocols.

Alternatively, the MACP amino acid sequence is analyzed using LASERGENE™ software (DNASTAR Inc.) to determine regions of high immunogenicity, and a corresponding oligopeptide is synthesized and used to raise antibodies by means known to those of skill in the art. Methods for selection of appropriate epitopes, such as those near the C-terminus or in hydrophilic regions are well described in the art. (See, e.g., Ausubel supra, ch. 11.)

Typically, oligopeptides 15 residues in length are synthesized using an Applied Biosystems Peptide Synthesizer Model 431A using fmoc-chemistry and coupled to KLH (Sigma, St. Louis, Mo.) by reaction with N-maleimidobenzoyl-N-hydroxysuccinimide ester (MBS) to increase immunogenicity. (See, e.g., Ausubel supra.) Rabbits are immunized with the oligopeptide-KLH complex in complete Freund's adjuvant. Resulting antisera are tested for antipeptide activity by, for example, binding the peptide to plastic, blocking with 1% BSA, reacting with rabbit antisera, washing, and reacting with radio-iodinated goat anti-rabbit IgG.

XIII. Purification of Naturally Occurring MACP Using Specific Antibodies

Naturally occurring or recombinant MACP is substantially purified by immunoaffinity chromatography using antibodies specific for MACP. An immunoaffinity column is constructed by covalently coupling anti-MACP antibody to an activated chromatographic resin, such as CNBr-activated Sepharose (Pharmacia & Upjohn). After the coupling, the resin is blocked and washed according to the manufacturer's instructions.

Media containing MACP are passed over the immunoaffinity column, and the column is washed under conditions that allow the preferential absorbance of MACP (e.g., high ionic strength buffers in the presence of detergent). The column is eluted under conditions that disrupt antibody/MACP binding (e.g., a buffer of pH 2 to pH 3, or a high concentration of a chaotrope, such as urea or thiocyanate ion), and MACP is collected.

XIV. Identification of Molecules which Interact with MACP

MACP, or biologically active fragments thereof, are labeled with $^{125}$I Bolton-Hunter reagent. (See, e.g. Bolton et al. (1973) Biochem. J. 133:529.) Candidate molecules previously arrayed in the wells of a multi-well plate are incubated with the labeled MACP, washed, and any wells with labeled MACP complex are assayed. Data obtained using different concentrations of MACP are used to calculate values for the number, affinity, and association of MACP with the candidate molecules.

Various modifications and variations of the described methods and systems of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

TABLE I

| Protein SEQ ID NO: | Nucleotide SEQ ID NO: | Clone ID | Library | Fragments |
|---|---|---|---|---|
| 1 | 6 | 370766 | LUNGNOT02 | 370766H1 (LUNGNOT02), 1443910H1 (THYRNOT03), 1807364F6 (SINTNOT13) |
| 2 | 7 | 1685090 | PROSNOT15 | 640134R1 (BRSTNOT03), 660500H1 (BRAINOT03), 663361H1 (BRAINOT03), 1685090H1 (PROSNOT15), 2722833H1 (LUNGTUT10) |
| 3 | 8 | 1820237 | GBLATUT01 | 318263F1 (EOSIHET02), 1473648T1 (LUNGTUT03), 1820237F6 (GBLATUT01), 1820237H1 (GBLATUT01), SBAA02402F1 |
| 4 | 9 | 1843956 | COLNNOT08 | 774971F1 (COLNNOT05), 1520270H1 (BLADTUT04), 1554785F1 (BLADTUT04), 1804118E6 (SINTNOT13), 1843956H1 (COLNNOT08), 2117449X11C1 (BRSTTUT02), 2117559X12C1 (BRSTTUT02), 2121391F6 (BRSTNOT07) |
| 5 | 10 | 2809903 | TLYMNOT06 | 2607564H1 (LUNGTUT07), 2748654H1 (LUNGTUT11), 2809903H1 (TLYMNOT06), 3034164F6 (TLYMNOT05) 3049055H1 (LUNGNOT25) |

TABLE 2

| Seq ID NO: | Amino Acid Residues | Potential Phosphorylation Sites | Potential glycosylation sites | Signature Sequence | Identification | Analytical Methods |
|---|---|---|---|---|---|---|
| 1 | 87 | S4 T27 S34 T38 S56 | | L32-L53 | dithiolethione-inducible gene-2 | BLAST |
| 2 | 379 | T319 S105 T215 S362 Y377 | N88 N245 | G285-S292 C198-C209 C230-C241 C262-C273 C294-C305 C326-C337 | 190 kd tenascin precursor | PRINTS BLOCKS |
| 3 | 140 | T116 T49 S121 | | | Tax interaction protein 33 | BLAST |
| 4 | 456 | S120 S288 S338 T416 | N34 N243 N304 | | placental protein Diff33 | BLAST |
| 5 | 235 | T37 S62 S205 S223 T48 T82 | N140 | M1-G19 C68-S96 C109-C147 L157-T175 L165-L186 C122-T129 | glucocorticoid induced TNFR family related protein precursor | BLAST BLOCKS PFAM SPScan MOTIFS |

TABLE 3

| Seq ID NO: | Tissue Expression (Fraction of Total) | Disease Class (Fraction of Total) | Vector |
|---|---|---|---|
| 6 | Cardiovascular (0.263) Nervous (0.211) Reproductive (0.211) | Proliferative (0.711) Inflammation (0.263) | >pBluescript |
| 7 | Cardiovascular (0.286) Reproductive (0.214) Nervous (0.143) | Proliferative (0.714) Inflammation (0.214) | >pINCY |
| 8 | Reproductive (0.276) Nervous (0.190) Cardiovascular (0.138) | Proliferative (0.845) Inflammation (0.120) | >pINCY |
| 9 | Reproductive (0.397) Gastrointestinal (0.247) Cardiovascular (0.096) | Proliferative (0.726) Inflammation (0.302) | >pSPORT |
| 10 | Hematopoietic/ Immune (0.500) Cardiovascular (0.333) | Proliferative (0.500) Inflammation (0.500) | >pINCY |

TABLE 4

| Clone ID | Library | Library Comment |
|---|---|---|
| 370766 | LUNGNOT02 | LUNGNOT02 pBluescript Library was constructed using RNA isolated from the lung tissue of a 47 year-old Caucasian male, who died of a subarachnoid hemorrhage. |
| 1685090 | PROSNOT15 | PROSNOT15 pINCY Library was constructed using RNA isolated from diseased prostate tissue removed from a 66 year-old Caucasian male during radical prostatectomy and regional lymph node excision. Pathology indicated adenofibromatous hyperplasia. Pathology for the associated tumor tissue indicated an adenocarcinoma (Gleason grade 2 + 3). The patient presented with elevated prostate specific antigen (PSA). Family history included prostate cancer, secondary bone cancer, and benign hypertension. |
| 1820237 | GBLATUT01 | GBLATUT01 pINCY Library was constructed using RNA isolated from gallbladder tumor tissue removed from a 78-year old Caucasian female during a cholecystectomy. Pathology indicated invasive grade 2 squamous cell carcinoma, forming a mass in the gallbladder. Patient history included diverticulitis of the colon, palpitations, benign hypertension, and hyperlipidemia. Family history included a cholecystectomy, atherosclerotic coronary artery disease, atherosclerotic coronary artery disease, hyperlipidemia, and benign hypertension. |
| 1843956 | COLNNOT08 | COLNNOT08 pSPORT1 Library was constructed using RNA isolated from colon tissue removed from a 60-year-old Caucasian male during a left hemicolectomy. |
| 2809903 | TLYMNOT06 | TLYMNOT06 pINCY Library was constructed using RNA isolated from activated Th2 cells. These cells were differentiated from umbilical cord CD4 T-cells with IL-4 in the presence of anti-IL-12 antibodies and B7-transfected COS cells, and then activated for six hours with anti-CD3 and anti-CD28 antibodies. |

TABLE 5

| Program | Description | Reference | Parameter Threshold |
|---|---|---|---|
| ABI FACTURA | A program that removes vector sequences and masks ambiguous bases in nucleic acid sequences. | Perkin-Elmer Applied Biosystems, Foster City. CA. | |
| ABI/ PARACEL FDF | A Fast Data Finder useful in comparing and annotating amino acid or nucleic acid sequences. | Perkin-Elmer Applied Biosystems, Foster City. CA; Paracel Inc., Pasadena, CA. | Mismatch < 50% |
| ABI Auto-Assembler | A program that assembles nucleic acid sequences. | Perkin-Elmer Applied Biosystems, Foster City. CA. | |

TABLE 5-continued

| Program | Description | Reference | Parameter Threshold |
|---|---|---|---|
| BLAST | A Basic Local Alignment Search Tool useful in sequence similarity search for amino acid and nucleic acid sequences. BLAST includes five functions: blastp, blastn, blastx, tblastn, and tblastx. | Altschul, S. F. et al. (1990) J. Mul. Biol. 215:403-410; Altschul, S. F. et al. (1997) Nucleic Acids Res. 25:3389-3402. | ESTs: Probability value = 1.0E−8 or less Full Length sequences: Probability value = 1.0E−10 or less |
| FASTA | A Pearson and Lipman algorithm that searches for similarity between a query sequence and a group of sequences of the same type. FASTA comprises as least five functions: fasta, tfasta, fastx, tfastx, and ssearch. | Pearson, W. R. and D. J. Lipman (1988) Proc. Natl. Acad Sci. 85:2444-2448; Pearson, W. R. (1990) Methods Enzymol. 183:63-98; and Smith. T. F. and M. S. Waterman (1981) Adv. Appl. Math. 2:482-489. | ESTs: fasta E value = 1.06E−6 Assembled ESTs: fasta Identity = 95% or greater and Match length = 200 bases or greater; fastx E value = 1.0E−8 or less Full Length sequences: fastx score = 100 or greater |
| BLIMPS | A BLocks IMProved Searcher that matches a sequence against those in BLOCKS and PRINTS databases to search for gene families, sequence homology, and structural fingerprint regions. | Henikoff, S and J. G. Henikoff, Nucl. Acid Res., 19:6565-72, 1991. J. G. Henikoff and S. Henikoff (1996) Methods Enzymol. 266:88-105; and Attwood, T. K. et al. (1997) J. Chem. Inf. Comput Sci. 37:417-424. | Score = 1000 or greater; Ratio of Score/Strength = 0.75 or larger; and Probability value = 1.0E−3 or less |
| HFAM | A Hidden Markov Models-based application useful for protein family search. | Krogh, A. et al. (1994) J. Mol. Biol., 235:1501-1531; Sonnhammer. E. L. L. et al. (1988) Nucleic Acids Res. 26:320-322. | Score = 10-50 bits, depending on individual protein families |
| ProfileScan | An algorithm that searches for structural and sequence motifs in protein sequences that match sequence patterns defined in Prosite. | Gribskov, M. et al. (1988) CABIOS 4:61-66, Gribskov, et al. (1989) Methods Enzymol. 183:146-159; Bairoch, A. et al. (1997) Nucleic Acids Res. 25:217-221. | Score = 4.0 or greater |
| Phred | A base-calling algorithm that examines automated sequencer traces with high sensitivity and probability. | Ewing, B. et al. (1998) Genome Res. 8:175-185; Ewing, B. and P. Green (1998) Genome Res. 8:186-194. | |
| Phrap | A Phils Revised Assembly Program including SWAT and CrossMatch, programs based on efficient implementation of the Smith-Waterman algorithm, useful in searching sequence homology and assembling DNA sequences. | Smith. T. F. and M. S. Waterman (1981) Adv. Appl. Math. 2:482-489; Smith, T. F. and M. S. Waterman (1981). Mol. Biol. 147:195-197; and Green, P., University of Washington. Seattle, WA. | Score = 120 or greater; Match length = 56 or greater |
| Consed | A graphical tool for viewing and editing Phrap assemblies | Gordon, D. et al. (1998) Genome Res. 8:195-202. | |
| SPScan | A weight matrix analysis program that scans protein sequences for the presence of secretory signal peptides. | Nielson, H. et al. (1997) Protein Engineering 10:1-6; Claverie. J. M. and S. Audic (1997) CABIOS 12:431-439. | Score = 5 or greater |
| Motifs | A program that searches amino acid sequences for patterns that matched those defined in Prosite. | Bairoch et al. supra; Wisconsin Package Program Manual, version 9, page M51-59. Genetics Computer Group, Madison, WI. | |

What is claimed is:

1. An isolated polynucleotide encoding a polypeptide comprising an amino acid sequence of SEQ ID NO:2.

2. An isolated polynucleotide which hybridizes under stringent conditions to the polynucleotide of claim 1, wherein said conditions comprise 37° C. in 500 mM NaCl, 50 mM trisodium citrate, 1% SDS, 35% formamide, and 100 µg/ml denatured salmon sperm DNA (ssDNA).

3. An isolated polynucleotide having a sequence which is complementary to the polynucleotide sequence of claim 1.

4. An isolated polynucleotide comprising SEQ ID NO:7.

5. An isolated polynucleotide having a sequence which is complementary to the polynucleotide of claim 4.

6. An expression vector comprising the polynucleotide of claim 1.

7. An isolated host cell comprising the expression vector of claim 6.

* * * * *

SEQUENCE LISTING

<160> NUMBER OF SEQ ID NOS: 10

<210> SEQ ID NO 1
<211> LENGTH: 87
<212> TYPE: PRT
<213> ORGANISM: Homo sapiens
<220> FEATURE:
<221> NAME/KEY: misc_feature
<223> OTHER INFORMATION: Incyte Clone No: 370766

<400> SEQUENCE: 1

```
Met Arg Glu Ser Ala Leu Glu Pro Gly Pro Val Pro Glu Ala Pro
  1               5                  10                  15

Ala Gly Gly Pro Val His Ala Val Thr Val Thr Leu Leu Glu
                 20                  25                  30

Lys Leu Ala Ser Met Leu Glu Thr Leu Arg Glu Arg Gln Gly Gly
                 35                  40                  45

Leu Ala Arg Arg Gln Gly Gly Leu Ala Gly Ser Val Arg Arg Ile
                 50                  55                  60

Gln Ser Gly Leu Gly Ala Leu Ser Arg Ser His Asp Thr Thr Ser
```

```
                     65                  70                  75
Asn Thr Leu Ala His Cys Trp Pro Arg Arg Ser Ala
                 80                  85

<210> SEQ ID NO 2
<211> LENGTH: 379
<212> TYPE: PRT
<213> ORGANISM: Homo sapiens
<220> FEATURE:
<221> NAME/KEY: misc_feature
<223> OTHER INFORMATION: Incyte Clone No: 1685090

<400> SEQUENCE: 2

Met Ala Arg Arg Ser Ala Phe Pro Ala Ala Leu Trp Leu Trp
  1               5                  10                  15

Ser Ile Leu Leu Cys Leu Leu Ala Leu Arg Ala Glu Ala Gly Pro
                 20                  25                  30

Pro Gln Glu Glu Ser Leu Tyr Leu Trp Ile Asp Ala His Gln Ala
                 35                  40                  45

Arg Val Leu Ile Gly Phe Glu Glu Asp Ile Leu Ile Val Ser Glu
                 50                  55                  60

Gly Lys Met Ala Pro Phe Thr His Asp Phe Arg Lys Ala Gln Gln
                 65                  70                  75

Arg Met Pro Ala Ile Pro Val Asn Ile His Ser Met Asn Phe Thr
                 80                  85                  90

Trp Gln Ala Ala Gly Gln Ala Glu Tyr Phe Tyr Glu Phe Leu Ser
                 95                 100                 105

Leu Arg Ser Leu Asp Lys Gly Ile Met Ala Asp Pro Thr Val Asn
                110                 115                 120

Val Pro Leu Leu Gly Thr Val Pro His Lys Ala Ser Val Val Gln
                125                 130                 135

Val Gly Phe Pro Cys Leu Gly Lys Gln Asp Gly Val Ala Ala Phe
                140                 145                 150

Glu Val Asp Val Ile Val Met Asn Ser Glu Gly Asn Thr Ile Leu
                155                 160                 165

Gln Thr Pro Gln Asn Ala Ile Phe Phe Lys Thr Cys Gln Gln Ala
                170                 175                 180

Glu Cys Pro Gly Gly Cys Arg Asn Gly Gly Phe Cys Asn Glu Arg
                185                 190                 195

Arg Ile Cys Glu Cys Pro Asp Gly Phe His Gly Pro His Cys Glu
                200                 205                 210

Lys Ala Leu Cys Thr Pro Arg Cys Met Asn Gly Gly Leu Cys Val
                215                 220                 225

Thr Pro Gly Phe Cys Ile Cys Pro Pro Gly Phe Tyr Gly Val Asn
                230                 235                 240

Cys Asp Lys Ala Asn Cys Ser Thr Thr Cys Phe Asn Gly Gly Thr
                245                 250                 255

Cys Phe Tyr Pro Gly Lys Cys Ile Cys Pro Pro Gly Leu Glu Gly
                260                 265                 270

Glu Gln Cys Glu Ile Ser Lys Cys Pro Gln Pro Cys Arg Asn Gly
                275                 280                 285

Gly Lys Cys Ile Gly Lys Ser Lys Cys Lys Cys Ser Lys Gly Tyr
                290                 295                 300

Gln Gly Asp Leu Cys Ser Lys Pro Val Cys Glu Pro Gly Cys Gly
                305                 310                 315
```

-continued

```
Ala His Gly Thr Cys His Glu Pro Asn Lys Cys Gln Cys Gln Glu
            320                 325                 330

Gly Trp His Gly Arg His Cys Asn Lys Arg Tyr Glu Ala Ser Leu
            335                 340                 345

Ile His Ala Leu Arg Pro Ala Gly Ala Gln Leu Arg Gln His Thr
            350                 355                 360

Pro Ser Leu Lys Lys Ala Glu Glu Arg Arg Asp Pro Pro Glu Ser
            365                 370                 375

Asn Tyr Ile Trp

<210> SEQ ID NO 3
<211> LENGTH: 140
<212> TYPE: PRT
<213> ORGANISM: Homo sapiens
<220> FEATURE:
<221> NAME/KEY: misc_feature
<223> OTHER INFORMATION: Incyte Clone No: 1820237

<400> SEQUENCE: 3

Met Asp Ser Arg Ile Pro Tyr Asp Asp Tyr Pro Val Val Phe Leu
  1               5                  10                  15

Pro Ala Tyr Glu Asn Pro Pro Ala Trp Ile Pro Pro His Glu Arg
             20                  25                  30

Val His His Pro Asp Tyr Asn Asn Glu Leu Thr Gln Phe Leu Pro
             35                  40                  45

Arg Thr Ile Thr Leu Lys Lys Pro Pro Gly Ala Gln Leu Gly Phe
             50                  55                  60

Asn Ile Arg Gly Gly Lys Ala Ser Gln Leu Gly Ile Phe Ile Ser
             65                  70                  75

Lys Val Ile Pro Asp Ser Asp Ala His Arg Ala Gly Leu Gln Glu
             80                  85                  90

Gly Asp Gln Val Leu Ala Val Asn Asp Val Asp Phe Gln Asp Ile
             95                 100                 105

Glu His Ser Lys Ala Val Glu Ile Leu Lys Thr Ala Arg Glu Ile
            110                 115                 120

Ser Met Arg Val Arg Phe Phe Pro Tyr Asn Tyr His Arg Gln Lys
            125                 130                 135

Glu Arg Thr Val His
            140

<210> SEQ ID NO 4
<211> LENGTH: 456
<212> TYPE: PRT
<213> ORGANISM: Homo sapiens
<220> FEATURE:
<221> NAME/KEY: misc_feature
<223> OTHER INFORMATION: Incyte Clone No: 1843956

<400> SEQUENCE: 4

Met Gly Ala Cys Leu Gly Ala Cys Ser Leu Leu Ser Cys Ala Ser
  1               5                  10                  15

Cys Leu Cys Gly Ser Ala Pro Cys Ile Leu Cys Ser Cys Cys Pro
             20                  25                  30

Ala Ser Arg Asn Ser Thr Val Ser Arg Leu Ile Phe Thr Phe Phe
             35                  40                  45

Leu Phe Leu Gly Val Leu Val Ser Ile Ile Met Leu Ser Pro Gly
             50                  55                  60

Val Glu Ser Gln Leu Tyr Lys Leu Pro Trp Val Cys Glu Glu Gly
```

-continued

```
                65                  70                  75
Ala Gly Ile Pro Thr Val Leu Gln Gly His Ile Asp Cys Gly Ser
                    80                  85                  90
Leu Leu Gly Tyr Arg Ala Val Tyr Arg Met Cys Phe Ala Thr Ala
                    95                 100                 105
Ala Phe Phe Phe Phe Phe Thr Leu Leu Met Leu Cys Val Ser Ser
                   110                 115                 120
Ser Arg Asp Pro Arg Ala Ala Ile Gln Asn Gly Phe Trp Phe Phe
                   125                 130                 135
Lys Phe Leu Ile Leu Val Gly Leu Thr Val Gly Ala Phe Tyr Ile
                   140                 145                 150
Pro Asp Gly Ser Phe Thr Asn Ile Trp Phe Tyr Phe Gly Val Val
                   155                 160                 165
Gly Ser Phe Leu Phe Ile Leu Ile Gln Leu Val Leu Leu Ile Asp
                   170                 175                 180
Phe Ala His Ser Trp Asn Gln Arg Trp Leu Gly Lys Ala Glu Glu
                   185                 190                 195
Cys Asp Ser Arg Ala Trp Tyr Ala Gly Leu Phe Phe Phe Thr Leu
                   200                 205                 210
Leu Phe Tyr Leu Leu Ser Ile Ala Ala Val Ala Leu Met Phe Met
                   215                 220                 225
Tyr Tyr Thr Glu Pro Ser Gly Cys His Glu Gly Lys Val Phe Ile
                   230                 235                 240
Ser Leu Asn Leu Thr Phe Cys Val Cys Val Ser Ile Ala Ala Val
                   245                 250                 255
Leu Pro Lys Val Gln Asp Ala Gln Pro Asn Ser Gly Leu Leu Gln
                   260                 265                 270
Ala Ser Val Ile Thr Leu Tyr Thr Met Phe Val Thr Trp Ser Ala
                   275                 280                 285
Leu Ser Ser Ile Pro Glu Gln Lys Cys Asn Pro His Leu Pro Thr
                   290                 295                 300
Gln Leu Gly Asn Glu Thr Val Val Ala Gly Pro Glu Gly Tyr Glu
                   305                 310                 315
Thr Gln Trp Trp Asp Ala Pro Ser Ile Val Gly Leu Ile Ile Phe
                   320                 325                 330
Leu Leu Cys Thr Leu Phe Ile Ser Leu Arg Ser Ser Asp His Arg
                   335                 340                 345
Gln Val Asn Ser Leu Met Gln Thr Glu Glu Cys Pro Pro Met Leu
                   350                 355                 360
Asp Ala Thr Gln Gln Gln Gln Gln Val Ala Ala Cys Glu Gly
                   365                 370                 375
Arg Ala Phe Asp Asn Glu Gln Asp Gly Val Thr Tyr Ser Tyr Ser
                   380                 385                 390
Phe Phe His Phe Cys Leu Val Leu Ala Ser Leu His Val Met Met
                   395                 400                 405
Thr Leu Thr Asn Trp Tyr Lys Pro Gly Glu Thr Arg Lys Met Ile
                   410                 415                 420
Ser Thr Trp Thr Ala Val Trp Val Lys Ile Cys Ala Ser Trp Ala
                   425                 430                 435
Gly Leu Leu Leu Tyr Leu Trp Thr Leu Val Ala Pro Leu Leu Leu
                   440                 445                 450
Arg Asn Arg Asp Phe Ser
                   455
```

-continued

```
<210> SEQ ID NO 5
<211> LENGTH: 235
<212> TYPE: PRT
<213> ORGANISM: Homo sapiens
<220> FEATURE:
<221> NAME/KEY: misc_feature
<223> OTHER INFORMATION: Incyte Clone No: 2809903

<400> SEQUENCE: 5

Met Gly Ala Phe Arg Ala Leu Cys Gly Leu Ala Leu Leu Cys Ala
 1               5                  10                  15

Leu Ser Leu Gly Gln Arg Pro Thr Gly Pro Gly Cys Gly Pro
            20                  25                  30

Gly Arg Leu Leu Leu Gly Thr Gly Thr Asp Ala Arg Cys Cys Arg
            35                  40                  45

Val His Thr Thr Arg Cys Cys Arg Asp Tyr Pro Gly Glu Glu Cys
            50                  55                  60

Cys Ser Glu Trp Asp Cys Met Cys Val Gln Pro Glu Phe His Cys
            65                  70                  75

Gly Asp Pro Cys Cys Thr Thr Cys Arg His His Pro Cys Pro Pro
            80                  85                  90

Gly Gln Gly Val Gln Ser Gln Gly Lys Phe Ser Phe Gly Phe Gln
            95                 100                 105

Cys Ile Asp Cys Ala Ser Gly Thr Phe Ser Gly Gly His Glu Gly
           110                 115                 120

His Cys Lys Pro Trp Thr Asp Cys Thr Gln Phe Gly Phe Leu Thr
           125                 130                 135

Val Phe Pro Gly Asn Lys Thr His Asn Ala Val Cys Val Pro Gly
           140                 145                 150

Ser Pro Pro Ala Glu Pro Leu Gly Trp Leu Thr Val Val Leu Leu
           155                 160                 165

Ala Val Ala Ala Cys Val Leu Leu Thr Ser Ala Gln Leu Gly
           170                 175                 180

Leu His Ile Trp Gln Leu Arg Ser Gln Cys Met Trp Pro Arg Glu
           185                 190                 195

Thr Gln Leu Leu Leu Glu Val Pro Pro Ser Thr Glu Asp Ala Arg
           200                 205                 210

Ser Cys Gln Phe Pro Glu Glu Glu Arg Gly Glu Arg Ser Ala Glu
           215                 220                 225

Glu Lys Gly Arg Leu Gly Lys Leu Trp Val
           230                 235

<210> SEQ ID NO 6
<211> LENGTH: 369
<212> TYPE: DNA
<213> ORGANISM: Homo sapiens
<220> FEATURE:
<221> NAME/KEY: misc_feature
<223> OTHER INFORMATION: Incyte Clone No: 370766

<400> SEQUENCE: 6
ggcccctgac cgtagtgcag ccagcagttg caggcagacg gagcagagcg gtcagggatc    60
atgagggaga gtgcgttgga gccggggcct gtgcccgagg cgccggcggg gggtcccgtg   120
cacgccgtga cggtggtgac cctgctggag aagctggcct ccatgctgga gactctgcgg   180
gagcggcagg gaggcctggc tcgaaggcag ggaggcctgg cagggtccgt gcgccgcatc   240
```

| | |
|---|---|
| cagagcggcc tgggcgctct gagtcgcagc cacgacacca ccagcaacac cttggcgcac | 300 |
| tgctggccaa ggcggagcgc gtgagctcgc acgccaacgc cgcccaagag cgcgcggtgc | 360 |
| gccgcgcac | 369 |

<210> SEQ ID NO 7
<211> LENGTH: 1415
<212> TYPE: DNA
<213> ORGANISM: Homo sapiens
<220> FEATURE:
<221> NAME/KEY: misc_feature
<223> OTHER INFORMATION: Incyte Clone No: 1685090

<400> SEQUENCE: 7

| | |
|---|---|
| tctaaacggg aacagccctg gctgagggag ctgcagcgca gcagagtatc tgacggcgcc | 60 |
| aggttgcgta ggtgcggcac gaggagtttt cccggcagcg aggaggtcct gagcagcatg | 120 |
| gcccggagga gcgccttccc tgccgccgcg ctctggctct ggagcatcct cctgtgcctg | 180 |
| ctggcactgc gggcggaggc cgggccgccg caggaggaga gcctgtacct atggatcgat | 240 |
| gctcaccagg caagagtact cataggattt gaagaagata tcctgattgt ttcagagggg | 300 |
| aaaatggcac cttttacaca tgatttcaga aaagcgcaac agagaatgcc agctattcct | 360 |
| gtcaatatcc attccatgaa ttttacctgg caagctgcag ggcaggcaga atacttctat | 420 |
| gaattcctgt ccttgcgctc cctggataaa ggcatcatgg cagatccaac cgtcaatgtc | 480 |
| cctctgctgg aacagtgcc tcacaaggca tcagttgttc aagttggttt cccatgtctt | 540 |
| ggaaaacagg atggggtggc agcatttgaa gtggatgtga ttgttatgaa ttctgaaggc | 600 |
| aacaccattc tccaaacacc tcaaaatgct atcttcttta aaacatgtca acaagctgag | 660 |
| tgcccaggcg ggtgccgaaa tggaggcttt tgtaatgaaa gacgcatctg cgagtgtcct | 720 |
| gatgggttcc acggacctca ctgtgagaaa gccctttgta ccccacgatg tatgaatggt | 780 |
| ggactttgtg tgactcctgg tttctgcatc tgcccacctg gattctatgg agtgaactgt | 840 |
| gacaaagcaa actgctcaac cacctgcttt aatggaggga cctgtttcta ccctggaaaa | 900 |
| tgtatttgcc ctccaggact agaggggag cagtgtgaaa tcagcaaatg cccacaaccc | 960 |
| tgtcgaaatg gaggtaaatg cattggtaaa agcaaatgta gtgttccaa aggttaccag | 1020 |
| ggagacctct gttcaaagcc tgtctgcgag cctggctgtg gtgcacatgg aacctgccat | 1080 |
| gaacccaaca atgccaatg tcaagaaggt tggcatggaa gacactgcaa taaaaggtac | 1140 |
| gaagccagcc tcatacatgc cctgaggcca gcaggcgccc agctcaggca gcacacgcct | 1200 |
| tcacttaaaa aggccgagga gcggcgggat ccacctgaat ccaattacat ctggtgaact | 1260 |
| ccgacatctg aaacgtttta agttacacca agttcatagc cttttgttaac ctttcatgtg | 1320 |
| ttgaatgttc aaataatgtt cattacactt aagaatactg gcctgaattt tattagcttc | 1380 |
| attataaatc actgagctga tatttactct tcctg | 1415 |

<210> SEQ ID NO 8
<211> LENGTH: 988
<212> TYPE: DNA
<213> ORGANISM: Homo sapiens
<220> FEATURE:
<221> NAME/KEY: misc_feature
<223> OTHER INFORMATION: Incyte Clone No: 1820237

<400> SEQUENCE: 8

| | |
|---|---|
| ggttcccaga ctgaattgtc agtgagcgga gtctgaggtc gctgtggact gcccactggg | 60 |
| ccttgcccga gatggacagc cggattcctt atgatgacta cccggtggtt ttcttgcctg | 120 |

| | |
|---|---|
| cctatgagaa tcctccagca tggattcctc ctcatgagag ggtacaccac ccggactaca | 180 |
| acaatgagtt gacccagttt ctgccccgaa ccatcacact gaagaagcct cctggagctc | 240 |
| agttgggatt taacatccga ggaggaaagg cctcccagct aggcatcttc atctccaagg | 300 |
| tgattcctga ctctgatgca catagagcag gactgcagga aggggaccaa gttctagctg | 360 |
| tgaatgatgt ggatttccaa gatattgagc acagcaaggc tgttgagatc ctgaagacag | 420 |
| ctcgtgaaat cagcatgcgt gtgcgcttct ttccctacaa ttatcatcgc caaaagaga | 480 |
| ggactgtgca ctagaaagtt gcagcccaca gcccttcatg tggactctgt catgacatgc | 540 |
| taactagact tcaggggagc cacttctgtt ttcagcccct ccctggaata gtgagttggg | 600 |
| aggatgggga gacagctaac caactgcatt acccaaacca tattgcactt ttagttccct | 660 |
| agttttctag gtgagcttca ttccctgaaa ggaggatgat gatatctagg cataacctag | 720 |
| cctgtgagga acctagttag gaaagacaac tgacatttat tgaatatcat gcactagtcc | 780 |
| cttacatatg tcatatttta attatagaaa tcagtagcaa aaagaatctt ggggattttc | 840 |
| catctgactt ccctggccat cttatcccat ccttgcacta tcagaagatt catacacttt | 900 |
| tgagactcca gtgagacgct gttttcaccc cttcctcctc ctagcctctc tcccaaaaag | 960 |
| taaaacacaa tgctgaagaa aaaaaaaa | 988 |

<210> SEQ ID NO 9
<211> LENGTH: 1905
<212> TYPE: DNA
<213> ORGANISM: Homo sapiens
<220> FEATURE:
<221> NAME/KEY: misc_feature
<223> OTHER INFORMATION: Incyte Clone No: 1843956

<400> SEQUENCE: 9

| | |
|---|---|
| gcgccccgcg cccggcgccg ggcgcccgaa gccgggagcc gccgccatgg gggcctgcct | 60 |
| gggagcctgc tccctgctca gctgcgcgtc ctgcctctgc ggctctgccc cctgcatcct | 120 |
| gtgcagctgc tgccccgcca gccgcaactc caccgtgagc cgcctcatct tcacgttctt | 180 |
| cctcttcctg ggggtgctgg tgtccatcat tatgctgagc ccgggcgtgg agagtcagct | 240 |
| ctacaagctg ccctgggtgt gtgaggaggg ggcggggatc cccaccgtcc tgcagggcca | 300 |
| catcgactgt ggctccctgc ttggctaccg cgctgtctac cgcatgtgct cgccacggc | 360 |
| ggccttcttc ttcttttca ccctgctcat gctctgcgtg agcagcagcc gggaccccg | 420 |
| ggctgccatc cagaatgggt tttggttctt taagttcctg atcctggtgg gcctcaccgt | 480 |
| gggtgccttc tacatccctg acggctcctt caccaacatc tggttctact tcggcgtcgt | 540 |
| gggctccttc ctcttcatcc tcatccagct ggtgctgctc atcgactttg cgcactcctg | 600 |
| gaaccagcgg tggctgggca aggccgagga gtgcgattcc cgtgcctggt acgcaggcct | 660 |
| cttcttcttc actctcctct tctacttgct gtcgatcgcg gccgtggcgc tgatgttcat | 720 |
| gtactacact gagcccagcg gctgccacga gggcaaggtc ttcatcagcc tcaacctcac | 780 |
| cttctgtgtc tgcgtgtcca tcgctgctgt cctgcccaag gtccaggacg cccagcccaa | 840 |
| ctcgggtctg ctgcaggcct cggtcatcac cctctacacc atgtttgtca cctggtcagc | 900 |
| cctatccagt atccctgaac agaaatgcaa ccccccatttg ccaacccagc tgggcaacga | 960 |
| gacagttgtg gcaggccccg agggctatga gacccagtgg tgggatgccc cgagcattgt | 1020 |
| gggcctcatc atcttcctcc tgtgcaccct cttcatcagt ctgcgctcct cagaccaccg | 1080 |
| gcaggtgaac agcctgatgc agaccgagga gtgcccacct atgctagacg ccacacagca | 1140 |

-continued

```
gcagcagcag caggtggcag cctgtgaggg ccgggccttt gacaacgagc aggacggcgt    1200
cacctacagc tactccttct tccacttctg cctggtgctg gcctcactgc acgtcatgat    1260
gacgctcacc aactggtaca agcccggtga gacccggaag atgatcagca cgtggaccgc    1320
cgtgtgggtg aagatctgtg ccagctgggc agggctgctc ctctacctgt ggaccctggt    1380
agccccactc ctcctgcgca accgcgactt cagctgaggc agcctcacag cctgccatct    1440
ggtgcctcct gccacctggt gcctctcggc tcggtgacag ccaacctgcc cctccccac    1500
accaatcagc caggctgagc ccccaccct gccccagctc caggacctgc ccctgagccg    1560
ggccttctag tcgtagtgcc ttcagggtcc gaggagcatc aggctcctgc agagcccat    1620
ccccccgcca cacccacacg gtggagctgc ctcttccttc ccctcctccc tgttgcccat    1680
actcagcatc tcggatgaaa gggctccctt gtcctcaggc tccacgggag cggggctgct    1740
ggagagagcg gggaactccc accacagtgg ggcatccggc actgaagccc tggtgttcct    1800
ggtcacgtcc cccaggggac cctgccccct tcctggactt cgtgccttac tgagtctcta    1860
agacttttc taataaacaa gccagtgcgt gtaccaaaaa aaaaa    1905
```

<210> SEQ ID NO 10
<211> LENGTH: 763
<212> TYPE: DNA
<213> ORGANISM: Homo sapiens
<220> FEATURE:
<221> NAME/KEY: misc_feature
<223> OTHER INFORMATION: Incyte Clone No: 2809903

<400> SEQUENCE: 10

```
agcacagcac ggggcgatgg gcgcgtttcg ggccctgtgc ggcctggcgc tgctgtgcgc     60
gctcagcctg ggtcagcgcc ccaccggggg tcccgggtgc ggccctgggc gcctcctgct    120
tgggacggga acggacgcgc gctgctgccg ggttcacacg acgcgctgct gccgcgatta    180
cccgggcgag gagtgctgtt ccgagtggga ctgcatgtgt gtccagcctg aattccactg    240
cggagaccct tgctgcacga cctgccggca ccacccttgt cccccaggcc agggggtaca    300
gtcccagggg aaattcagtt ttggcttcca gtgtatcgac tgtgcctcgg ggaccttctc    360
cgggggccac gaaggccact gcaaaccttg acagactgc acccagttcg ggtttctcac    420
tgtgttccct gggaacaaga cccacaacgc tgtgtgcgtc ccagggtccc cgccggcaga    480
gccgcttggg tggctgaccg tcgtcctcct ggccgtggcc gcctgcgtcc tcctcctgac    540
ctcggcccag cttggactgc acatctgcta gctgaggagt cagtgcatgt ggccccgaga    600
gacccagctg ctgctggagg tgccgccgtc gaccgaagac gccagaagct gccagttccc    660
cgaagaagaa cggggcgagc gatcggcaga ggagaagggg cggctgggga aactgtgggt    720
gtgagcctgg ccgtccttcg gggccacgac cgcagcagcc ctt    763
```